(12) United States Patent
Allen et al.

(10) Patent No.: US 6,495,528 B1
(45) Date of Patent: Dec. 17, 2002

(54) 2-(PURIN-9-YL)-TETRAHYDROFURAN-3,4-DIOL DERIVATIVES

(75) Inventors: David George Allen, Stevenage (GB); Chuen Chan, Stevenage (GB); Richard Peter Charles Cousins, Stevenage (GB); Brian Cox, Stevenage (GB); Joanna Victoria Geden, Aston Science Park (GB); Heather Hobbs, Stevenage (GB); Suzanne Elaine Keeling, Stevenage (GB); Alison Judith Redgrave, Stevenage (GB); Thomas Davis Roper, IV, Apex, NC (US); Shiping Xie, Cary, NC (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/720,390

(22) PCT Filed: Jun. 23, 1999

(86) PCT No.: PCT/EP99/04269

§ 371 (c)(1),
(2), (4) Date: Feb. 20, 2001

(87) PCT Pub. No.: WO99/67265

PCT Pub. Date: Dec. 29, 1999

(30) Foreign Application Priority Data

Jun. 23, 1998 (GB) .............................. 9813538
Apr. 23, 1999 (GB) .............................. 9909482

(51) Int. Cl.$^7$ .................. A61L 31/70; C07H 19/167
(52) U.S. Cl. ................ 514/46; 514/45; 514/47; 514/48; 514/885; 536/4.1; 536/17.2; 536/17.3; 536/18.5; 536/27.21; 536/27.61; 536/27.8; 536/27.81
(58) Field of Search ................ 514/45, 46, 47, 514/48, 885; 536/4.1, 17.2, 17.3, 18.5, 27.21, 27.6, 27.8, 27.81

(56) References Cited

U.S. PATENT DOCUMENTS

| 3,796,700 A | 3/1974 | Yoshioka et al. |
| 3,864,483 A | 2/1975 | Stein et al. |
| 3,966,917 A | 6/1976 | Prasad et al. |
| 3,983,104 A | 9/1976 | Vorbruggen |
| 4,167,565 A | 9/1979 | Stein et al. |
| 4,224,438 A | 9/1980 | Fauland et al. |
| 4,663,313 A | 5/1987 | Bristol et al. |
| 4,704,381 A | 11/1987 | Schaumann et al. |
| 4,767,747 A | 8/1988 | Hamilton et al. |
| 4,855,288 A | 8/1989 | Gadient et al. |
| 4,962,194 A | 10/1990 | Bridges |
| 4,968,697 A | 11/1990 | Hutchison |
| 4,985,409 A | 1/1991 | Yamada et al. |
| 5,043,325 A | 8/1991 | Olsson et al. |
| 5,106,837 A | 4/1992 | Carson et al. |
| 5,153,318 A | 10/1992 | Rideout et al. |
| 5,219,839 A | 6/1993 | Bru-Magniez et al. |
| 5,219,840 A | 6/1993 | Gadient et al. |
| 5,364,862 A | 11/1994 | Spada et al. |
| 5,424,297 A | 6/1995 | Rubio et al. |

FOREIGN PATENT DOCUMENTS

| DE | 26 21 470 | 5/1976 |
| EP | 0 066 918 | 12/1982 |
| EP | 0 139 358 | 5/1985 |
| EP | 0 161 128 | 11/1985 |
| EP | 0 181 129 | 5/1986 |
| EP | 0 222 330 | 5/1987 |
| EP | 0 232 813 | 8/1987 |
| EP | 0 253 962 | 1/1988 |
| EP | 0 277 917 | 8/1988 |
| EP | 0 423 776 | 4/1991 |
| EP | 0 423 777 | 4/1991 |
| GB | 1386 656 | 3/1975 |
| GB | 1399 670 | 7/1975 |
| GB | 2 203 149 | 10/1988 |
| JP | 58167599 | 10/1983 |
| JP | 58174322 | 10/1983 |
| WO | 86/00310 | 1/1986 |
| WO | 88/03147 | 5/1988 |
| WO | 88/03148 | 5/1988 |
| WO | 92/05177 | 4/1992 |
| WO | 93/14102 | 7/1993 |
| WO | 94/02497 | 2/1994 |
| WO | WO 94 17090 A | 8/1994 |
| WO | 94/18215 | 8/1994 |
| WO | 95/02604 | 1/1995 |
| WO | 95/11904 | 5/1995 |
| WO | 95/18817 | 7/1995 |
| WO | 96/02543 | 2/1996 |
| WO | 96/02553 | 2/1996 |
| WO | 98/01426 | 1/1998 |
| WO | WO 98 01459 A | 1/1998 |
| WO | 98/16539 | 4/1998 |
| WO | WO 99 28319 A | 7/1998 |
| WO | WO 99 38877 A | 8/1999 |
| WO | WO 99 41267 A | 8/1999 |
| WO | 91/13082 | 9/2001 |

OTHER PUBLICATIONS

J.J. Baker, et. al., "5'-Substituted-5'-Deoxy Nucleosides," *Tetrahedron*, 1974 vol. 30, pp 2939 to 2942.

Mester, et. al., "Mode of Action of Some Oxidized Sugar Derivatives of Adenine on Platelet Aggregation," *Pathologie–Biologie*, 20, Suppl., pp 11–14, Dec. 1972.

*Primary Examiner*—James O. Wilson

(57) ABSTRACT

A series of 2-(Purin-9-yl)-tetrahydrofuran-3,4-diol derivatives with broad anti-inflammatory properties which inhibit leukocyte recruitment and activation and which are agonists of the adenosine 2a receptor are described.

26 Claims, No Drawings

2-(PURIN-9-YL)-TETRAHYDROFURAN-3,4-DIOL DERIVATIVES

This application is filed pursuant to 35 U.S.C. §371 as a United States National Phase Application of International Application No. PCT/EP99/04269 filed Jun. 23, 1999, which claims priority from GB9813538.7 filed Jun. 23, 1998 and GB9909482.3 filed Apr. 23, 1999.

This invention relates to new chemical compounds, processes for their preparation, pharmaceutical formulations containing them and their use in therapy.

Inflammation is a primary response to tissue injury or microbial invasion and is characterised by leukocyte adhesion to the endothelium, diapedesis and activation within the tissue. Leukocyte activation can result in the generation of toxic oxygen species (such as superoxide anion), and the release of granule products (such as peroxidases and proteases). Circulating leukocytes include neutrophils, eosinophils, basophils, monocytes and lymphocytes. Different forms of inflammation involve different types of infiltrating leukocytes, the particular profile being regulated by the profile of adhesion molecule, cytokine and chemotactic factor expression within the tissue.

The primary function of leukocytes is to defend the host from invading organisms such as bacteria and parasites. Once a tissue is injured or infected a series of events occurs which causes the local recruitment of leukocytes from the circulation into the affected tissue. Leukocyte recruitment is controlled to allow for the orderly destruction and phagocytosis of foreign or dead cells, followed by tissue repair and resolution of the inflammatory infiltrate. However in chronic inflammatory states, recruitment is often inappropriate, resolution is not adequately controlled and the inflammatory reaction causes tissue destruction.

There is evidence from both in vitro and in vivo studies to suggest that compounds active at the adenosine A2a receptor will have anti-inflammatory actions. The area has been reviewed by Cronstein (1994). Studies on isolated neutrophils show an A2 receptor-mediated inhibition of superoxide generation, degranulation, aggregation and adherence (Cronstein et al, 1983 and 1985; Burkey and Webster, 1993; Richter, 1992; Skubitz et al, 1988. When agents selective for the A2a receptor over the A2b receptor (eg CGS21680) have been used, the profile of inhibition appears consistent with an action on the A2a receptor subtype (Dianzani et al, 1994). Adenosine agonists may also downregulate other classes of leucocytes (Elliot and Leonard, 1989; Peachell et al, 1989). Studies on whole animals have shown the anti-inflammatory effects of methotrexate to be mediated through adenosine and A2 receptor activation (Asako et al, 1993; Cronstein et al, 1993 and 1994). Adenosine itself, and compounds that raise circulating levels of adenosine also show anti-inflammatory effects in vivo (Green et al, 1991; Rosengren et al, 1995). In addition raised levels of circulating adenosine in man (as a result of adenosine deaminase deficiency) results in immunosuppression (Hirschorn, 1993).

Certain substituted 4'-carboxamido and 4'-thioamido adenosine derivatives which are useful for the treatment of inflammatory diseases are described in international Patent Application Nos. WO94/17090, WO96/02553, WO96/02543 (Glaxo Group). Substituted 4'-carboxamidoadenosine derivatives useful in the treatment of dementia are described in AU 8771946 (Hoechst Japan). Substituted 4'-hydroxymethyl adenosine derivatives which are useful for the treatment of gastrointestinal motility disorders are described in EP-A-423776 and EP-A-423777 (Searle). Substituted 4'-hydroxymethyl adenosine derivatives which are useful as platelet aggregation inhibitors are described in BE-768925 (Takeda). 4'-Hydroxymethyl adenosine derivatives and 4'-esters thereof which are useful as antihypertensive agents or have other cardiovascular activity are described in U.S. Pat. No. 4,663,313, EP 139358 and U.S. Pat. No. 4,767,747 (Warner Lambert), U.S. Pat. No. 4,985,409 (Nippon Zoki) and U.S. Pat. No. 5,043,325 (Whitby Research). 4-Hydroxymethyladenosine derivatives useful in the treatment of autoimmune disorders are described in U.S. Pat. No. 5,106,837 (Scripps Research Institute). 4'-Hydroxymethyladenosine derivatives useful as anti-allergic agents are described in U.S. Pat. No. 4,704,381 (Boehringer Mannheim). Certain 4'-tetrazolylalkyl adenosine derivatives which are useful in the treatment of heart and circulatory disorders are generically described in DT-A-2621470 (Pharma-Waldhof). Other 4'-carboxamidoadenosine derivatives useful in the treatment of cardiovascular conditions are described in U.S. Pat. No. 5,219,840, GB 2203149 and GB 2199036 (Sandoz), WO94102497 (US Dept. Health), U.S. Pat. No. 4,968,697 and EP 277917 (Ciba Geigy), U.S. Pat. No. 5,424,297 (Univ. Virginia) and EP 232813 (Warner Lambert). Other 4'-carboxamidoadenosine derivatives lacking substitution on the purine ring in the 2-position are described in DT 2317770, DT 2213180, U.S. Pat. Nos. 4,167,565, 3,864,483 and 3,966,917 (Abbott Labs), DT 2034785 (Boehringer Mannheim), JP 58174322 and JP 58167599 (Tanabe Seiyaku), WO92/05177 and U.S. Pat. No. 5,364,862 (Rhone Poulenc Rorer), EP 66918 (Procter and Gamble), WO86/00310 (Nelson), EP 222330, U.S. Pat. No. 4,962,194, WO88/03147 and WO88/03148 (Warner Lambert) and U.S. Pat. No. 5,219,839, WO95/18817 and WO93/14102 (Lab UPSA). 4'-Hydroxymethyladenosine derivatives lacking substitution on the purine ring in the 2-position are described in WO95/11904 (Univ Florida). 4'-Substituted adenosine derivatives useful as adenosine kinase inhibitors are described in WO94/18215 (Gensia). Other 4'-halomethyl, methyl, thioalkylmethyl or alkoxymethyl adenosine derivatives are described in EP 161128 and EP 181129 (Warner Lambert) and U.S. Pat. No. 3,983,104 (Schering). Other 4'-carboxamidoadenosine derivatives are described in U.S. Pat. No. 7,577,528 (NIH), WO91/13082 (Whitby Research) and WO95/02604 (US Dept Health).

Certain tetrazole containing deoxynucleotides which were found to lack anti-infective activity are described in Baker et al (1974) Tetrahedron 30, 2939–2942. Other tetrazole containing adenosine derivatives which show activity as platelet aggregation inhibitors are described in Mester and Mester (1972) Pathologie-Biologie, 20 (Suppl) 11–14. Certain nitrile containing ribose derivatives are described in Schmidt et al (1974) Liebigs. Ann. Chem. 1856–1863.

Other publications include: WO 98/16539 (Novo Nordisk A/S) which describes adenosine derivatives for the treatment of myocardial and cerebral ischaemia and epilepsy; WO 98/01426 (Rhone-Poulenc Rorer Pharmaceuticals Inc.) which relates to adenosine derivatives possessing antihypertensive, cardioprotective, anti-ischaemic and anti-lipolytic properties; and WO 98/01459 (Novo Nordisk A/S) which describes N,9-disubstituted adenine derivatives which are substituted in the 4' position by unsubstituted oxazolyl or isoxazolyl and the use of such compounds for the treatment of disorders involving cytokines in humans. WO 98/28319 (Glaxo Group Limited) was published subsequent to the earliest priority date of this application and describes 4'-substituted tetrazole 2-(purin-9-yl)-tetrahydrofuran-3,4-diol derivatives.

We have now found a novel group of compounds with broad anti-inflammatory properties which inhibit leukocyte recruitment and activation and which are agonists of the adenosine 2a receptor. The compounds are therefore of potential therapeutic benefit in providing protection from leukocyte-induced tissue damage in diseases where leukocytes are implicated at the site of inflammation. The compounds of the invention may also represent a safer alternative to corticosteroids in the treatment of inflammatory diseases, whose uses may be limited by their side-effect profiles.

More particularly, the compounds of this invention may show an improved profile over known A2a-selective agonists in that they generally lack significant agonist activity at the human A3 receptor. This profile can be considered of benefit as A3 receptors are also found on leukocytes (eg eosinophil) and other inflammatory cells (eg mast cell) and activation of these receptors may have pro-inflammatory effects (Kohno et al, 1996; Van Schaick et al 1996). It is even considered that the bronchoconstrictor effects of adenosine in asthmatics may be mediated via the adenosine A3 receptor (Kohno et al, 1996).

Thus, according to the invention we provide compounds of formula (I):

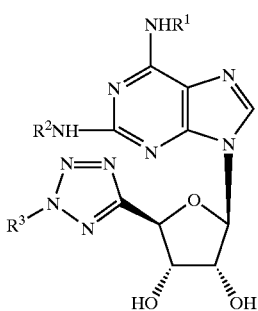

(I)

wherein
$R^1$ and $R^2$ independently represent a group selected from:
(i) $C_{3-8}$cycloalkyl-;
(ii) hydrogen;
(iii) aryl$_2$CHCH$_2$—;
(iv) $C_{3-8}$cycloalkyl$C_{1-6}$alkyl-;
(v) $C_{1-8}$alkyl-;
(vi) aryl$C_{1-6}$alkyl-;
(vii) $R^4R^5N$—$C_{1-6}$alkyl-;
(viii) $C_{1-6}$alkyl-CH(CH$_2$OH)—;
(ix) aryl$C_{1-5}$alkyl-CH(CH$_2$OH)—;
(x) aryl$C_{1-5}$alkyl-C(CH$_2$OH)$_2$—;
(xi) $C_{3-8}$cycloalkyl independently substituted by one or more (e.g. 1, 2 or 3) —(CH$_2$)$_p$R$^6$ groups;
(xii) H$_2$NC(=NH)NHC$_{1-6}$alkyl-;
(xiii) a group of formula

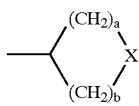

or such a group in which one methylene carbon atom adjacent to X, or both if such exist, is substituted by methyl;
(xiv) —$C_{1-6}$alkyl-OH;
(xv) —$C_{1-8}$haloalkyl;

(xvi) a group of formula

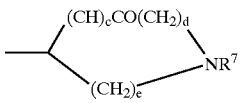

(xvii) aryl; and
(xviii) —(CH$_2$)$_f$SO$_2$NH$_g$(C$_{1-4}$alkyl-)$_{2-g}$ or —(CH$_2$)$_f$SO$_2$NH$_g$(arylC$_{1-4}$alkyl-)$_{2-g}$;
$R^3$ represents methyl, ethyl, —CH=CH$_2$, n-propyl, —CH$_2$CH=CH$_2$, —CH=CHCH$_3$, isopropyl, isopropenyl, cyclopropyl, cyclopropenyl, cyclopropylmethyl, cyclopropenylmethyl, cyclobutyl, cyclobutenyl, —(CH$_2$)$_q$halogen, —(CH$_2$)$_h$Y(CH$_2$)$_i$H, —(CH$_2$)$_h$COOCH$_3$, —(CH$_2$)$_h$OCOCH$_3$, —(CH$_2$)$_h$CON(CH$_2$)$_m$H((CH$_2$)$_n$H), —(CH$_2$)$_h$CO(CH$_2$)$_o$H or —CH$_2$C((CH$_2$)$_u$H)=NO(CH$_2$)$_v$H;
Y represents O, S or N(CH$_2$)$_j$;
a and b independently represent an integer 0 to 4 provided that a+b is in the range 3 to 5;
c, d and e independently represent an integer 0 to 3 provided that c+d+e is in the range 2 to 3;
f represents 2 or 3 and g represents an integer 0 to 2;
p represents 0 or 1;
q represents 2 or 3;
h represents 2 or 3;
i represents an integer 0 to 2 such that h+i is in the range 2 to 4
j represents an integer 0 to 2 such that h+i+j is in the range 2 to 4
m and n independently represent an integer 0 to 2 such that m+n is in the range 0 to 2;
o represents an integer 0 to 2 such that h+o is in the range 2 to 3;
u and v independently represent 0 or 1 such that u+v is in the range 0 to 1;
$R^4$ and $R^5$ independently represent hydrogen, $C_{1-6}$alkyl, aryl, aryl$C_{1-6}$alkyl- or $NR^4R^5$ together may represent pyrrolidinyl, piperidinyl, morpholinyl, azetidinyl, azepinyl, piperazinyl or N—$C_{1-6}$alkylpiperazinyl.
$R^6$ represents OH, NH$_2$, NHCOCH$_3$ or halogen;
$R^7$ represents hydrogen, $C_{1-6}$alkyl, $C_{1-6}$alkylaryl or —COC$_{1-6}$alkyl;
X represents NR$^7$, O, S, SO or SO$_2$;
provided that when $R^3$ represents methyl, ethyl or isopropyl then $R^1$ and/or $R^2$ independently must represent:
(a) —(CH$_2$)$_f$SO$_2$NH$_g$(C$_{1-4}$alkyl-)$_{2-g}$ or —(CH$_2$)$_f$SO$_2$NH$_g$(arylC$_{1-4}$alkyl-)$_{2-g}$ where f is 2 or 3 and g is an integer 0 to 2;
(b) $C_{3-8}$cycloalkyl independently substituted by one or more —(CH$_2$)$_p$NHCOCH$_3$ groups;
(c) a group of formula

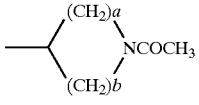

or such a group in which one methylene carbon atom adjacent to X, or both if such exist, is substituted by methyl;

(d) a group of formula

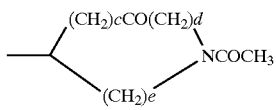

and salts and solvates thereof.

References to $C_{1-6}$alkyl include references to an aliphatic hydrocarbon grouping containing 1 to 6 carbon atoms which may be straight chain or branched and may be saturated or unsaturated although will be preferably saturated. References to $C_{1-4}$alkyl, $C_{1-5}$alkyl, $C_{2-4}$alkyl and $C_{1-8}$alkyl may be interpreted similarly.

References to aryl include references to mono- and bicyclic carbocyclic aromatic rings (e.g. phenyl, naphthyl) and heterocyclic aromatic rings containing 1–3 hetero atoms selected from N, O and S (e.g. pyridinyl, pyrimidinyl, thiophenyl, imidazolyl, quinolinyl, furanyl, pyrrolyl, oxazolyl) all of which may be optionally substituted, e.g. by $C_{1-6}$alkyl, halogen, hydroxy, nitro, $C_{1-6}$alkoxy, cyano, amino, $SO_2NH_2$ or —$CH_2OH$.

Examples of $C_{3-8}$cycloalkyl for $R^1$ and $R^2$ include monocyclic alkyl groups (e.g. cyclopentyl, cyclohexyl) and bicyclic alkyl groups (e.g. norbornyl such as exo-norborn-2-yl).

Examples of $(aryl)_2CHCH_2$— for $R^1$ and $R^2$ include $Ph_2CHCH_2$— or such a group in which one or both phenyl moieties is substituted, e.g. by halogen or $C_{1-4}$alkyl. Examples of $C_{3-8}$cycloalkyl$C_{1-6}$alkyl- for $R^1$ and $R^2$ include ethylcyclohexyl. Examples of $C_{1-8}$-alkyl for $R^1$ and $R^2$ include —$(CH_2)_2C(Me)_3$, —$CH(Et)_2$ and $CH_2$=$C(Me)CH_2CH_2$—.

Examples of aryl$C_{1-6}$alkyl- for $R^1$ and $R^2$ include —$(CH_2)_2Ph$, —$CH_2Ph$ or either in which Ph is substituted (one or more times) by halogen (e.g. iodine), amino, methoxy, hydroxy, —$CH_2OH$ or $SO_2NH_2$; —$(CH_2)_2$ pyridinyl (e.g. —$(CH_2)_2$pyridin-2-yl) optionally substituted by amino; $(CH_2)_2$imidazolyl or this group in which imidazolyl is N-substituted by $C_{1-6}$alkyl (especially methyl).

Examples of $R^4R^5N$—$C_{1-6}$alkyl- for $R^1$ and $R^2$ include ethyl-piperidin-1-yl, ethyl-pyrrolidin-1-yl, ethyl-morpholin-1-yl, —$(CH_2)_2NH(pyridin$-2-yl) and —$(CH_2)_2NH_2$. Examples of $C_{1-6}$alkyl-$CH(CH_2OH)$— for $R^1$ and $R^2$ include $Me_2CHCH(CH_2OH)$—. Examples of aryl$C_{1-5}$alkyl-$CH(CH_2OH)$— for $R^1$ and $R^2$ include $PhCH_2CH(CH_2OH)$— especially

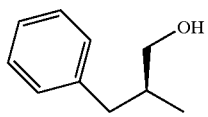

Examples of aryl $C_{1-5}$alkyl-$C(CH_2OH)_2$— for $R^1$ and $R^2$ include $PhCH_2C(CH_2OH)_2$—. Examples of $C_{3-8}$ cycloalkyl independently substituted by one or more —$(CH_2)_pR^6$ groups (eg 1, 2 or 3 such groups) for $R^1$ and $R^2$ include 2-hydroxy-cyclopentyl and 4-aminocyclohexyl (especially trans-4-amino-cyclohexyl).

Examples of $H_2NC(=NH)NHC_{1-6}$alkyl for $R^1$ and $R^2$ include $H_2NC(=NH)NH(CH_2)_2$—.

Examples of groups of formula

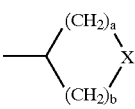

for $R^1$ and $R^2$ include pyrrolidin-3-yl, piperidin-3-yl, piperidin-4-yl or a derivative in which the ring nitrogen is substituted by $C_{1-6}$alkyl (e.g. methyl) or benzyl, tetrahydro-1,1-dioxide thiophen-3-yl, tetrahydropyran-4-yl, tetrahydrothiopyran-4-yl and 1,1-dioxo-hexahydro-1.lamda.6-thiopyran-4-yl.

Examples of —$C_{1-6}$alkyl-OH groups for $R^1$ and $R^2$ include —$CH_2CH_2OH$.

Examples of $C_{1-8}$haloalkyl for $R^1$ and $R^2$ include —$CH_2CH_2Cl$ and $(CH_3)_2ClC(CH_2)_3$—.

Examples of groups of formula

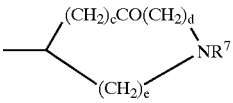

for $R^1$ and $R^2$ include 2-oxo-pyrrolidin-4-yl, 2-oxo-pyrrolidin-5-yl or a derivative in which the ring nitrogen is substituted by $C_{1-6}$alkyl (e.g. methyl) or benzyl.

Examples of aryl for $R^1$ and $R^2$ include phenyl optionally substituted by halogen (e.g. fluorine, especially 4-fluorine).

Examples of $C_{1-6}$alkyl for $R^7$ include methyl and $C_{1-6}$alkylaryl for $R^7$ include benzyl. Examples of $COC_{1-6}$ alkyl for $R^7$ include —$COCH_3$.

Examples of $C_{1-5}$alkyl for $R^3$ include n-propyl and allyl. An example of $C_{3-4}$ cycloalkyl for $R^3$ includes cyclobutyl. An example of —$(CH_2)_hO(CH_2)_iH$ for $R^3$ includes —$(CH_2)_2OMe$. Examples of $C_{2-4}$alkyl substituted by halogen or hydroxy include —$(CH_2)_2Cl$, —$(CH_2)_2OH$ and —$(CH_2)_3OH$.

We prefer that $R^1$ and $R^2$ do not both represent hydrogen.

We prefer $R^1$ to represent aryl$_2CHCH_2$—, $C_{1-8}$alkyl, hydrogen or aryl $C_{1-6}$alkyl-.

We particularly prefer $R^1$ to represent $Ph_2CHCH_2$—, —$CH(Et)_2$, hydrogen or phenylethyl-, especially $Ph_2CHCH_2$—.

We prefer $R^2$ to represent $R^4R^5N$—$C_{1-6}$alkyl-, aryl$C_{1-6}$alkyl-, aryl$C_{1-5}$alkylCH(CH_2OH)$—, aryl $C_{1-6}$ alkyl or $C_{1-6}$ alkyl-$CH(CH_2OH)$—.

We particularly prefer $R^2$ to represent $(CH_2)_2(piperidin-1-yl)$, 2-(1-methyl-1H-imidazol-4yl)ethyl, 1S-hydroxymethyl-2-phenylethyl, phenylethyl or 1S-hydroxymethyl-2-methyl propyl, especially —$(CH_2)_2(piperidin-1-yl)$.

We prefer $R^3$ to represent $C_{1-3}$alkyl (including n-propyl and 2-propenyl), cyclobutyl, cyclopropylmethyl, —$(CH_2)_2OCOCH_3$, —$(CH_2)_{2-3}OH$ or —$(CH_2)_2$halogen. More preferably $R^3$ represents n-propyl, 2-propenyl, cyclobutyl, cyclopropylmethyl, —$(CH_2)_2OCOCH_3$, or —$(CH_2)_{2-3}OH$.

We particularly prefer $R^3$ to represent —$(CH_2)_2OCOCH_3$, —$(CH_2)_2OH$ or $(CH_2)_3OH$, especially —$(CH_2)_2OCOCH_3$ or —$(CH_2)_2OH$, most especially —$(CH_2)_2OH$.

We prefer $R^4$ and $R^5$ independently to represent hydrogen, $C_{1-6}$alkyl or aryl or $NR^4R^5$ together to represent pyrrolidinyl, piperidinyl, morpholinyl, azetidinyl, azepinyl, piperazinyl or N-methylpiperazinyl;

We prefer X to represent $NR^7$, O, S or $SO_2$, particularly $NR^7$ or $SO_2$, especially $NR^7$.

We prefer that a and b both represent 2 or that a represents 1 and b represents 2.

We prefer that $R^7$ represents hydrogen.

We prefer that p represents 0. We prefer q to represent 2. We prefer h to represent 2. We prefer i to represent 0 or 1, especially 0. We prefer j to represent 1. We prefer m and n to represent 0 or 1. We prefer o to represent 1.

We prefer u and v to represent 0.

We prefer that $R^6$ represents OH or $NH_2$ especially $NH_2$.

We prefer that c represents 0 and either d represents 2 and e represents 0 or d represents 1 and e represents 1.

The representation of formula (I) indicates the absolute stereochemistry at positions around the tetrahydrofuran ring. When sidechains contain chiral centres the invention extends to mixtures of enantiomers (including racemic mixtures) and diastereoisomers as well as to individual enantiomers. Generally it is preferred to use a compound of formula (I) in the form of a purified single enantiomer.

We also provide a process for preparation of compounds of formula (I) which comprises:

(a) reacting a corresponding compound of formula (II)

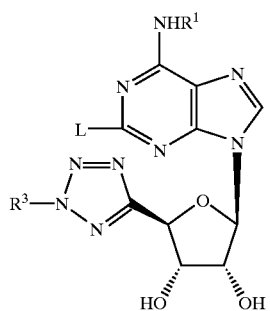

(II)

wherein L represents a leaving group or a protected derivative thereof with a compound of formula $R^2NH_2$ or a protected derivative thereof;

(b) preparing a compound of formula (I) in which $R^1$ represents hydrogen by reducing a compound of formula (III)

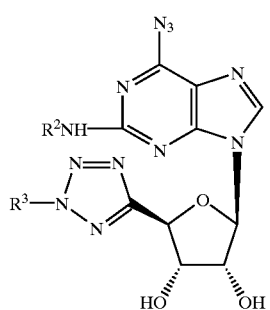

(III)

or a protected derivative thereof; or (c) deprotecting a compound of formula (I) which is protected; and where desired or necessary converting a compound of formula (I) or a salt thereof into another salt thereof.

In process (a) L represents a leaving group such as halogen eg chlorine or fluorine. The reaction of process (a) will generally be carried out on heating the reagents to a temperature of 50° C.–150° C. in the presence of a solvent such as DMSO. Preferably an organic base, e.g. a trisubstituted organic amine (such as diisopropylethylamine) is also present for the reaction. Under these conditions we particularly prefer that Hal represents fluorine (especially when $R^1$ represents hydrogen) since the reaction has a tendency to proceed rapidly with high efficiency.

In process (b) the reduction reaction may be performed by catalytic hydrogenation, e.g. over Pd/C under standard conditions.

In process (c) examples of protecting groups and the means for their removal can be found in T W Greene "Protective Groups in Organic Synthesis" (J Wiley and Sons, 1991). Suitable hydroxyl protecting groups include alkyl (e.g. methyl), acetal (e.g. acetonide) and acyl (e.g. acetyl or benzoyl) which may be removed by hydrolysis, and arylalkyl (e.g. benzyl) which may be removed by catalytic hydrogenolysis. Suitable amine protecting groups include sulphonyl (e.g. tosyl), acyl e.g. benzyloxycarbonyl or t-butoxycarbonyl) and arylalkyl (e.g. benzyl) which may be removed by hydrolysis or hydrogenolysis as appropriate.

Suitable salts of the compounds of formula (I) include physiologically acceptable salts such as acid addition salts derived from inorganic or organic acids, for example hydrochlorides, hydrobromides, 1-hydroxy-2-naphthoates, mesylates, sulphates, phosphates, acetates, benzoates, citrates, succinates, lactates, tartrates, fumarates and maleates, and if appropriate, inorganic base salts such as alkali metal salts, for example sodium salts. Other salts of the compounds of formula (I) include salts which may not be physiologically acceptable but may be useful in the preparation of compounds of formula (I) and physiologically acceptable salts thereof. Examples of such salts include trifluoroacetates and formates.

Examples of suitable solvates of the compounds of formula (I) include hydrates.

Acid-addition salts of compounds of formula (I) may be obtained by treating a free-base of formula (I) with an appropriate acid.

The compounds of formula (II) or a protected derivative thereof may be prepared by reacting a compound of IV

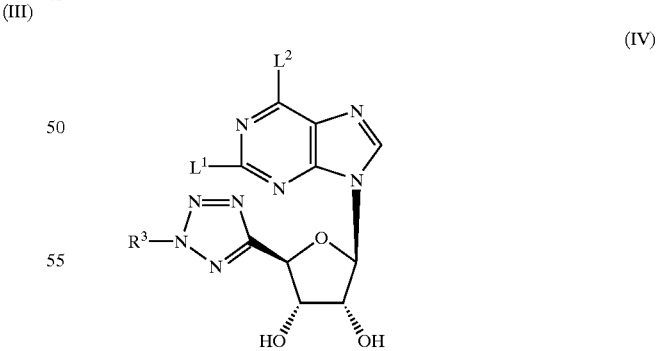

(IV)

or a protected derivative thereof with a compound of formula $R^1NH_2$. $L^1$ and $L^2$ independently represent a leaving group such as halogen eg chlorine or fluorine. This reaction will preferably be performed in the presence of a base such as an organic amine base (e.g. diisopropyl ethylamine) in a solvate such as an alcohol (e.g. isopropanol) at elevated temperature (e.g. reflux).

Compounds of formula (III) or a protected derivative thereof may be prepared by reacting a compound of formula (IIIA)

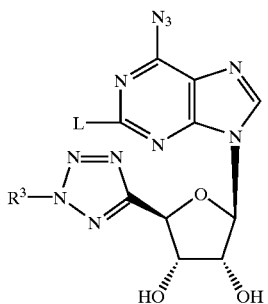

(IIIA)

wherein L represents a leaving group such as halogen eg chlorine or fluorine, or a protected derivative thereof, with a compound of formula $R^2NH_2$ under conventional conditions.

Compounds of formula (IIIA), or a protected derivative thereof, may be prepared by reacting a compound of formula (IV), or a protected derivative thereof, with an azide, e.g. sodium azide under conventional conditions.

The compound of formula (IV) or a protective derivative thereof may be prepared by reacting a compound of formula (V)

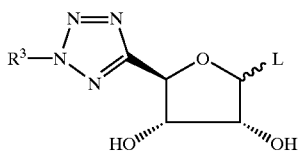

(V)

wherein L represents a leaving group or a protected derivative thereof with a 2,6,dihalopurine, e.g. 2,6-dichloropurine.

We prefer to use the compound of formula (V) wherein the ribose 2- and 3-hydroxyl groups are protected, e.g. by acetyl. Leaving group L may represent OH but will preferably represent $C_{1-6}$alkoxy (e.g. methoxy or ethoxy), an ester moiety (e.g. acetyloxy or benzoyloxy) or halogen. The preferred group L is acetyloxy. The reaction may be performed by combining the reactants in an inert solvent such as MeCN in the presence of a Lewis Acid (eg TMSOTf) and DBU and warming to, say, 70–80° C.

Compounds of formula (V) may be prepared from a compound of formula (VI)

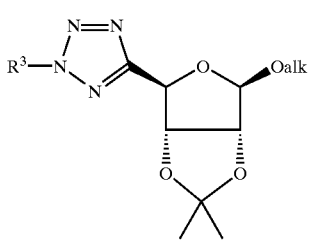

(VI)

wherein alk represents $C_{1-6}$ alkyl eg methyl by treating the compound of formula (VI) with trifluoroacetic acid in water followed by reprotection, e.g. by reaction with acetic anhydride in pyridine.

Compounds of formula (V) in which L represents halogen, may be prepared from the corresponding 1'-alcohol or a 1'-ester such as the acetate. Reaction will generally occur on treatment with anhydrous HCl or HBr. 1'-iodides may be prepared directly on treatment with trimethylsilyliodide and 1'-fluorides may be prepared on treatment with DAST. An inert solvent eg diethylether, DCM, THF or CCl$_4$ will generally be suitable.

Compound of formula (VI) may be prepared following Scheme 1:

Scheme 1

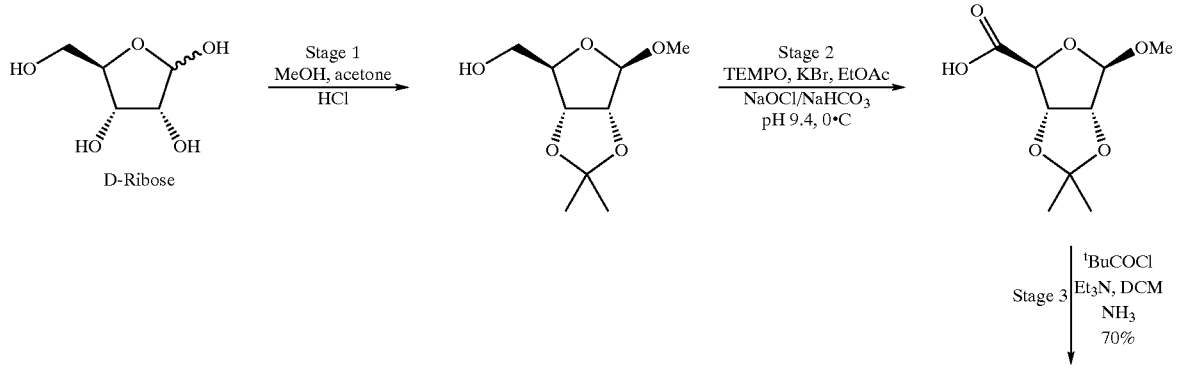

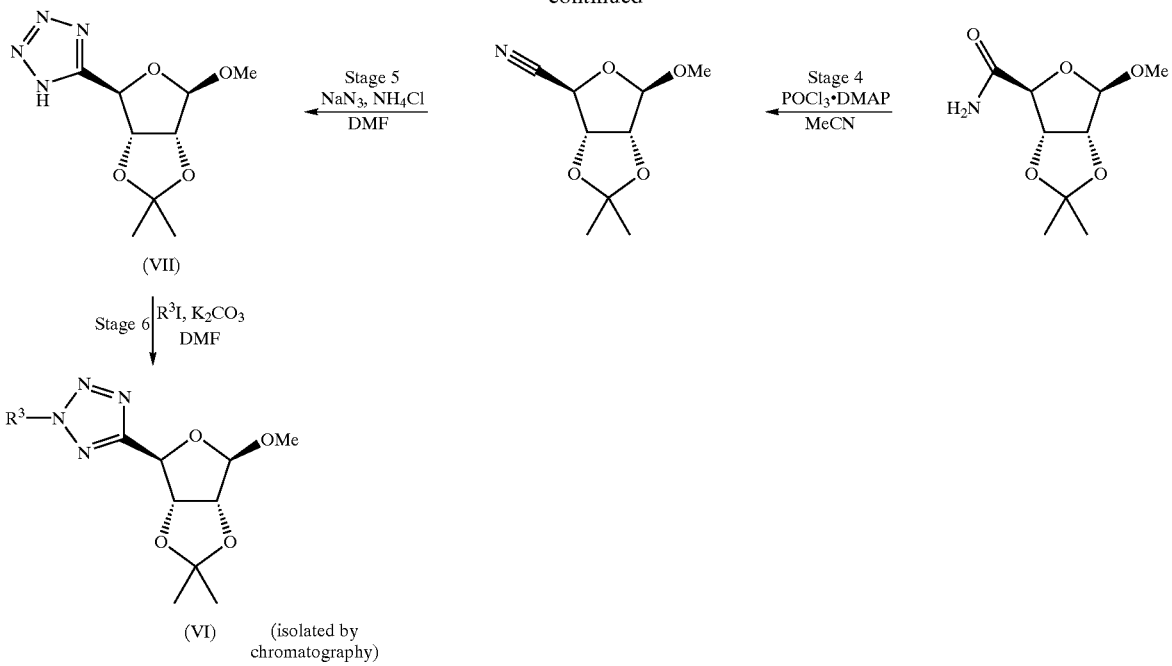

General conditions for Stages 1–6 will be known to persons skilled in the art. It will also be appreciated that the reagents and conditions set out in Scheme 1 are example conditions and alternative reagents and conditions for achieving the same chemical transformation may be known to persons skilled in the art. For example an alternative alcohol, e.g. a $C_{1-6}$alkyl alcohol may be used in Stage 1 to give a different $C_{1-6}$ alkyloxy leaving group in compounds of formula (VII) and (VI). Stage 1 may also be modified in that the use of HCl can be substituted by perchloric acid ($HClO_4$) and 2,2 dimethoxypropane, or alternatively acetyl chloride (which has the advantage that it maintains high yield and avoids use of perchlorate salts). Alternative reaction conditions can be used in Stage 3, which may utilise ethyl acetate, thionyl chloride and gaseous ammonia (which has the advantage that it avoids chlorinated solvent and the synthesis of troublesome ammonium pivaloate impurity). Stage 4 may also be performed using $POCl_3$, TEA, DMF and ethyl acetate in the reaction conditions (which avoids the use of hazardous DMAP). Compounds of formula (VII) wherein a leaving group besides OMe is desired may be prepared by analogy with the method described above for preparation of compounds of formula (V). Alternative groups may be used to protect the 2' and 3' hydroxy groups on the ribose in Stage 1. We have also found that Stage 5 may desirably be performed using azidotrimethylsilane and dibutyltin oxide in toluene.

Following stage 6, the impure product may be purified using conventional techniques, and especially using flash chromatography conditions under nitrogen pressure. We have found that satisfactory conditions include loading the impure product in a minimum volume of dichloromethane onto a Keiselgel 60 (Merck 9385) column and eluting using a gradient solvent system with ethyl acetate (10–40%) in cyclohexane.

Compounds of formula (II), and protected derivatives thereof, may also be prepared by reacting a compound of formula (V), or a protected derivative thereof with a compound of formula (VIII)

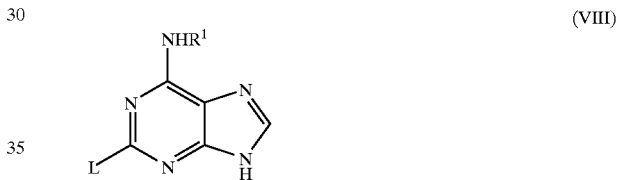

(VIII)

wherein L represents a leaving group such as halogen, e.g. chlorine or fluorine optionally followed by a deprotection or deprotection and reprotection reaction.

We prefer to use compounds of formula (V) in protected form. In particular we prefer that at least the hydroxy group in the 2-position on the ribose is protected as an ester group, e.g. by acetyl or benzoyl since this has a tendency to result in greater stereoselectivity in the coupling reaction. We prefer that the 2- and 3-position hydroxy groups are protected by acetyl. Suitable leaving groups L are a described previously. The preferred leaving group L is acetyloxy.

This process is particularly preferred when L represents fluorine (and most especially when $R^1$ represents hydrogen) since the reaction is generally fast and efficient and the reaction has a tendency to produce products of high crystallinity.

The product of this reaction may be deprotected if desired under conventional conditions eg on treatment with an alcohol (eg isopropanol) under mild basic conditions (eg in the presence of potassium carbonate).

The reaction of compounds of formula (V) (in protected form) and compounds of formula (VIII) may be performed in the presence of a Lewis Acid (eg TMSOTf) and optionally a silylating agent (eg BSA) in an inert solvent such as acetonitrile followed by work-up eg with water. When L represents halogen the Lewis Acid can generally be omitted when a silylating agent is present.

Certain compounds of formula (VIII) are known. Other compounds of formula (VIII) may be prepared by reaction of a compound of formula (IX)

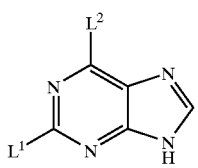

wherein L¹ and L² independently represent a leaving group such as halogen, e.g. chlorine or fluorine,
with R¹NH₂ under conventional conditions.

Compounds of formula R¹NH₂, R²NH₂ and IX are either known or may be prepared by conventional methods known per se.

As a further aspect of the invention we also provide new process which may be used to provide compounds of formula (I) without the proviso.

Thus we provide a process for preparation of a compound of formula (I) without the proviso which comprises
(d) reacting a corresponding compound of formula (X)

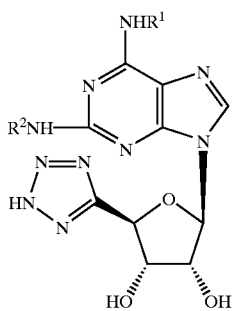

with a compound of formula (XI)
R³—L (XI)
wherein L is a leaving group; or (e) reacting a corresponding compound of formula (XII)

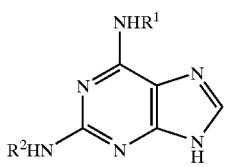

with a compound of formula (V) or a protected derivative thereof.

Process (d) will generally take place on combining the two reagents in the presence of a mild base e.g. $K_2CO_3$ and an inert organic solvent eg DMF. Typical leaving groups L include halogen (e.g. Br).

Process (e) will generally take place in the presence of a Lewis Acid (e.g. TMSOTf) and optionally a silylating agent (e.g. BSA) in an inert solvent such as MeCN followed by work-up e.g. with water. We prefer L to represent acetyloxy and the two hydroxy groups to be protected as the acetyl ester. A deprotection step (using mild base e.g. $K_2CO_3$) will then be necessary to generate the compound of formula (I).

Compounds of formula (X) may be prepared by analogous methods to those described above for the preparation of compounds of formula (I). When compounds of formula (X) are prepared via the analogues of compounds of formula (II), (III), (IIIA) and/or (IV) in which R³ is replaced by hydrogen, such compounds are preferably protected in the N2-position of the tetrazole. A suitable protecting group is benzyl which may be incorporated by treating the unprotected tetrazole with a benzyl halide (e.g. benzyl bromide) in the presence of base (e.g. $K_2CO_3$). An illustrative process for the preparation of compounds of formula (X) is given in Scheme 2:

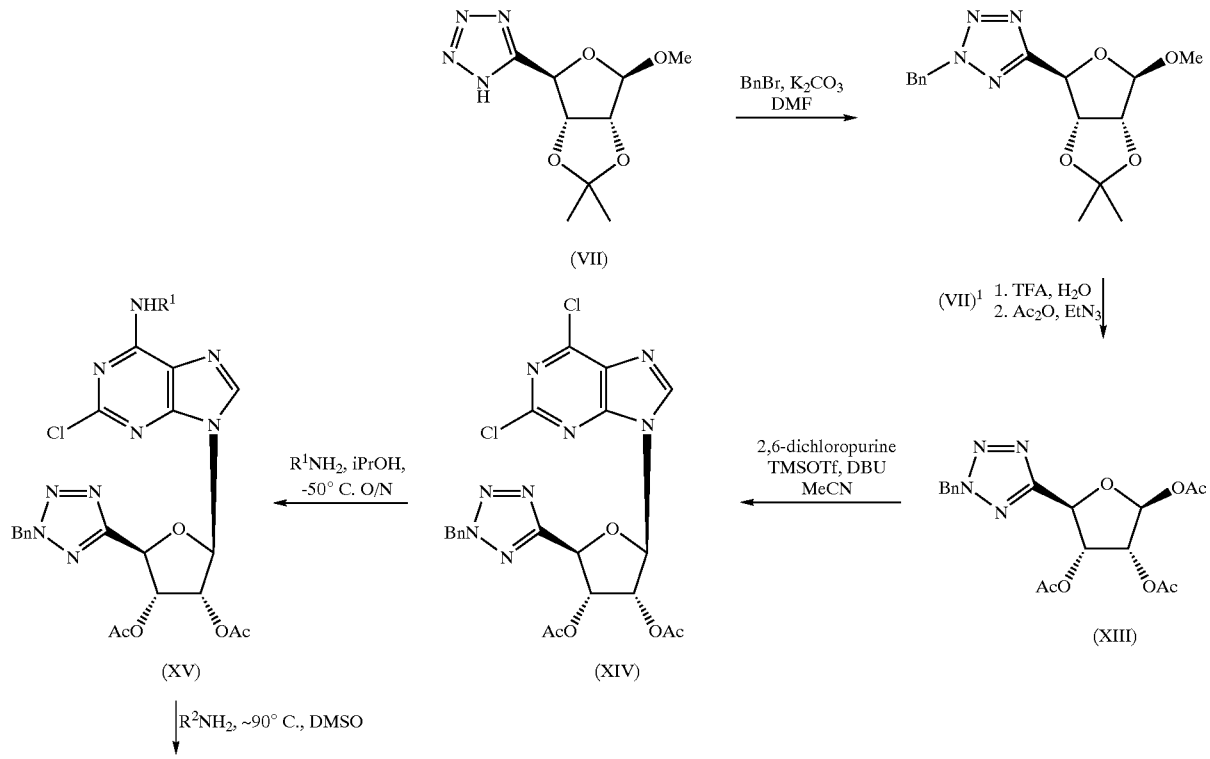

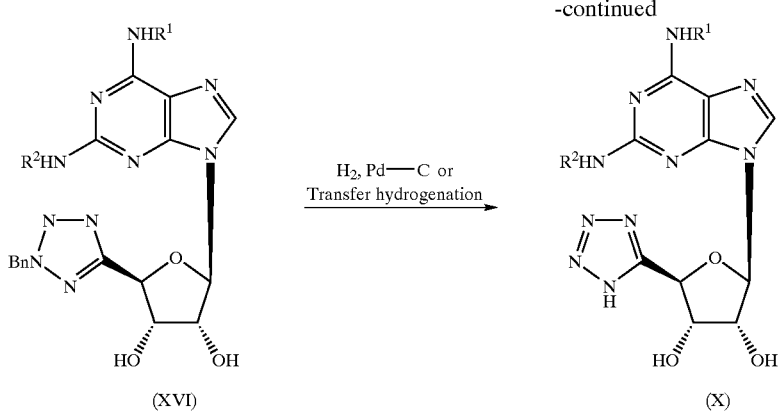

Compounds of formula (XI) are known or may be prepared by known methods.

Compounds of formula (XII) may be prepared, for example following Scheme 3:

Scheme 3

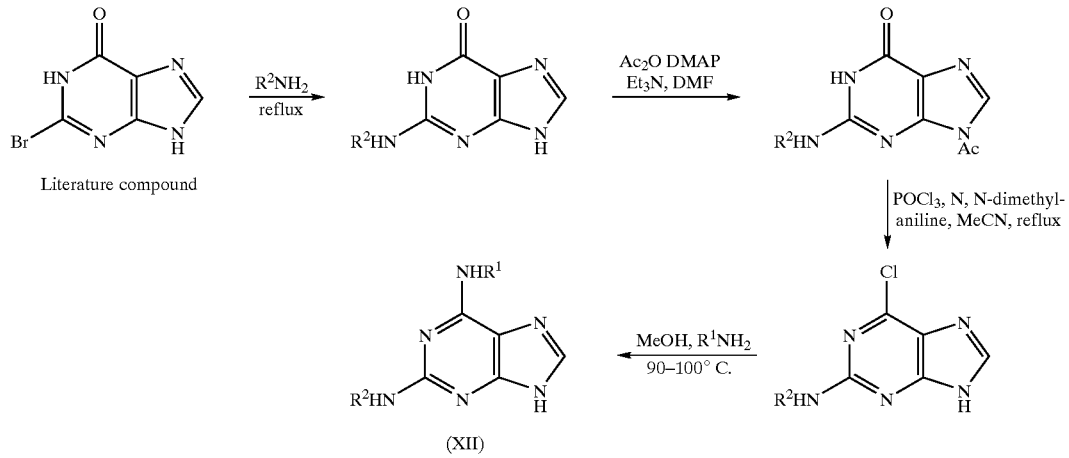

Processes (d) and (e) are particularly suitable for preparing the compound (2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol and salts and solvates thereof, especially the maleate salt.

We prefer process (e).

The potential for compounds of formula (I) to inhibit leukocyte function may be demonstrated, for example, by their ability to inhibit superoxide ($O_2$—) generation from neutrophils stimulated with chemoattractants such as N-formylmethionyl-leucyl-phenylalanine (fMLP). Accordingly, compounds of formula (I) are of potential therapeutic benefit in providing protection from leukocyte-induced tissue damage in diseases where leukocytes are implicated at the site of inflammation.

Examples of disease states in which the compounds of the invention have potentially beneficial anti-inflammatory effects include diseases of the respiratory tract such as adult respiratory distress syndrome. (ARDS), bronchitis (including chronic bronchitis), cystic fibrosis, asthma (including allergen-induced asthmatic reactions), chronic obstructive pulmonary disease (COPD), emphysema, rhinitis and septic shock. Other relevant disease states include diseases of the gastrointestinal tract such as intestinal inflammatory diseases including inflammatory bowel disease (e.g. Crohn's disease or ulcerative colitis), *Helicobacter-pylori* induced gastritis and intestinal inflammatory diseases secondary to radiation exposure or allergen exposure, and non-steroidal anti-inflammatory drug-induced gastropathy. Furthermore, compounds of the invention may be used to treat skin diseases such as psoriasis, allergic dermatitis and hypersensitivity reactions and diseases of the central nervous system which have an inflammatory component eg Alzheimer's disease and multiple sclerosis.

Further examples of disease states in which compounds of the invention have potentially beneficial effects include cardiac conditions such as peripheral vascular disease, post-ischaemic reperfusion injury and idiopathic hypereosinophilic syndrome.

Compounds of the invention which inhibit lymphocyte function may be useful as immunosuppressive agents and so have use in the treatment of auto-immune diseases such as rheumatoid arthritis and diabetes.

Compounds of the invention may also be useful in inhibiting metastasis.

Diseases of principal interest include asthma and COPD.

It will be appreciated by those skilled in the art that reference herein to treatment extends to prophylaxis as well as the treatment of established conditions.

As mentioned above, compounds of formula (I) are useful in human or veterinary medicine, in particular as anti-inflammatory agents.

There is thus provided as a further aspect of the invention a compound of formula (I) or a physiologically acceptable salt or solvate thereof for use in human or veterinary medicine, particularly in the treatment of patients with inflammatory conditions who are susceptible to leukocyte-induced tissue damage.

According to another aspect of the invention, there is provided the use of a compound of formula (I) or a physiologically acceptable salt or solvate thereof for the manufacture of a medicament for the treatment of patients with inflammatory conditions who are susceptible to leukocyte-induced tissue damage.

In a further or alternative aspect there is provided a method for the treatment of a human or animal subject with an inflammatory condition who is susceptible to leukocyte-induced tissue damage, which method comprises administering to said human or animal subject an effective amount of a compound of formula (I) or a physiologically acceptable salt or solvate thereof.

The compounds according to the invention may be formulated for administration in any convenient way, and the invention therefore also includes within its scope pharmaceutical compositions for use in anti-inflammatory therapy, comprising a compound of formula (I) or a physiologically acceptable salt or solvate thereof together, if desirable, with one or more physiologically acceptable diluents or carriers.

There is also provided a process for preparing such a pharmaceutical formulation which comprises mixing the ingredients.

The compounds according to the invention may, for example, be formulated for oral, buccal, parenteral, topical or rectal administration, preferably for parenteral or topical (e.g. by aerosol) administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

By topical administration as used herein, we include administration by insufflation and inhalation. Examples of various types of preparation for topical administration include ointments, creams, lotions, powders, pessaries, sprays, aerosols, capsules or cartridges for use in an inhaler or insufflator, solutions for nebulisation or drops (e.g. eye or nose drops).

Ointments and creams may, for example, be formulated with an aqueous or oily base with the addition of suitable thickening and/or gelling agents and/or solvents. Such bases may thus, for example, include water and/or an oil such as liquid paraffin or a vegetable oil such as arachis oil or castor oil or a solvent such as a polyethylene glycol. Thickening agents which may be used include soft paraffin, aluminium stearate, cetostearyl alcohol, polyethylene glycols, microcrystalline wax and beeswax.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents or suspending agents.

Spray compositions may be formulated, for example, as aqueous solutions or suspensions or as aerosols delivered from pressurised packs, with the use of a suitable propellant, e.g. dichlorodifluoromethane, trichlorofluoromethane, dichlorotetra-fluoroethane, 1,1,1,2,3,3,3-heptafluoropropane, 1,1,1,2-tetrafluoroethane, carbon dioxide or other suitable gas.

Intranasal sprays may be formulated with aqueous or non-aqueous vehicles with the addition of agents such as thickening agents, buffer salts or acid or alkali to adjust the pH, isotonicity adjusting agents or anti-oxidants.

Capsules and cartridges of for example gelatin, or blisters of for example laminated aluminium foil, for use in an inhaler or insufflator may be formulated containing a powder mix of a compound of the invention and a suitable powder base such as lactose or starch.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

The pharmaceutical compositions according to the invention may also be used in combination with other therapeutic agents, for example anti-inflammatory agents (such as corticosteroids (eg fluticasone propionate, beclomethasone dipropionate, mometasone furoate, triamcinolone acetonide or budesonide) or NSAIDs (eg sodium cromoglycate)) or beta adrenergic agents (such as salmeterol, salbutamol, formoterol, fenoterol or terbutaline and salts thereof) or antiinfective agents (eg antibiotics, antivirals).

The invention thus provides, in a further aspect, a combination comprising a compound of formula (I) or a physiologically acceptable salt or solvate thereof together with another therapeutically active agent, for example an anti-inflammatory agent such as a corticosteroid or NSAID.

The combination referred to above may conveniently be presented for use in the form of a pharmaceutical formulation and thus pharmaceutical formulations comprising a combination as defined above together with a physiologically acceptable diluent or carrier thereof represent a further aspect of the invention.

The individual components of such combinations may be administered either sequentially or simultaneously in separate or combined pharmaceutical formulations. Appropriate doses of known therapeutic agents will be readily appreciated by those skilled in the art.

Compounds of the invention may conveniently be administered in amounts of, for example, 0.01 to 500 mg/kg body weight, preferably 0.01 to 100 mg/kg body weight, 1 to 4 times daily. The precise dose will of course depend on the age and condition of the patient and the particular route of administration chosen.

The compounds of the invention have the advantage that they may be more efficacious, show greater selectivity, have fewer side effects, have a longer duration of action, be more bioavailable by the preferred route, show less systemic activity when administered by inhalation or have other more desirable properties than similar known compounds.

In particular the compounds of the invention have the advantage that they may show greater selectivity for the adenosine 2a receptor subtype over other adenosine receptor subtypes (especially the A1 and A3 receptor subtypes) than hitherto known compounds.

As a further aspect of the invention we provide certain compounds as new and useful intermediates.

Compounds of the invention may be tested for in vitro and in vivo biological activity in accordance with the following screens:

(1) Agonist activity against adenosine 2a, adenosine 1 and adenosine 3 receptor subtypes.

Agonist selectivity of compounds against other human adenosine receptors is determined using Chinese hamster ovary (CHO) cells transfected with the gene for the relevant human adenosine receptor following a method based on that of Castanon and Spevak, 1994. The CHO cells are also transfected with cyclic AMP response elements promoting the gene for secreted placental alkaline phosphatase (SPAP) (Wood, 1995). The effect of test compounds is determined by their effects on basal levels of cAMP (A2a) or on forskolin-enhanced cAMP (A1 and A3) as reflected by changes in levels of SPAP. $EC_{50}$ values for compounds are then determined as a ratio to that of the non-selective agonist N-ethyl carboxamide adenosine (NECA).

(2) Antigen-induced lung eosinophil accumulation in sensitised guinea pigs.

Ovalbumin sensitised guinea pigs are dosed with mepyramine (1 mg/kg ip) to protect against anaphylactic bronchospasm. A compound of the invention is then given by the inhaled route (30 min breathing of an aerosol of the compound) immediately prior to ovalbumin challenge (30 min breathing of an aerosol generated from a 50 ug/ml solution of ovalbumin). Twenty four hours after challenge, the guinea pigs are killed and the lungs lavaged. Total and differential leukocyte counts are then obtained for the bronchoalveolar lavage fluid and the dose of test compound giving a 50% reduction in eosinophil accumulation ($ED_{50}$) is determined (Sanjar et al. 1992).

REFERENCES

Asako H, Wolf, R E, Granger, D N (1993), Gastroenterology 104, pp 31–37;
Burkey T H, Webster, R O, (1993), Biochem. Biophys Acta 1175, pp 312–318;
Castanon M J, Spevak W, (1994), Biochem. Biophys Res. Commun. 198, pp 626–631;
Cronstein B N, Kramer S B, Weissmann G, Hirschhorn R, (1983), Trans. Assoc. Am. Physicians 96, pp 384–91;
Cronstein B N, Kramer S B, Rosenstein E D, Weissmann G, Hirschhorn R, (1985), Ann N.Y. Acad. Sci. 451, pp 291–301;
Cronstein B N, Naime D, Ostad E, (1993), J. Clin. Invest. 92, pp 2675–82;
Cronstein B N, Naime D, Ostad E, (1994), Adv. Exp. Med. Biol., 370, pp 411–6;
Cronstein B N, (1994), J. Appl. Physiol. 76, pp 5–13;
Dianzani C, Brunelleschi S, Viano I, Fantozzi R, (1994), Eur. J. Pharmacol 263, pp 223–226;
Elliot K R F, Leonard E J, (1989), FEBS Letters 254, pp 94–98;
Green P G, Basbaum A I, Helms C, Levine J D, (1991), Proc. Natl. Acad Sci. 88, pp 4162–4165;
Hirschorn R, (1993), Pediatr. Res 33, pp S35–41;
Kohno Y; Xiao-duo J; Mawhorter S D; Koshiba M; Jacobson K A. (1996).Blood 88 p3569–3574.
Peachell P T, Lichtenstein L M, Schleimer R P, (1989), Biochem Pharmacol 38, pp 1717–1725;
Richter J, (1992), J. Leukocyte Biol. 51, pp 270–275;
Rosengren S, Bong G W, Firestein G S, (1995), J. Immunol. 154, pp 5444–5451;
Sanjar S, McCabe P J, Fattah D, Humbles M, Pole S M, (1992), Am. Rev. Respir. Dis. 145, A40;
Skubitz K M, Wickman N W, Hammerschmidt D E, (1988), Blood 72, pp 29–33
Van Schaick E A; Jacobson K A; Kim H O; Ijzerman A P; Danhof M. (1996) Eur J Pharmacol 308 p311–314.
Wood K V. (1995) Curr Opinion Biotechnology 6 p50–58.

The invention is illustrated by the following Examples:

EXAMPLES

General Experimental Details

Where products were purified by column chromatography, 'flash silica' refers to silica gel for chromatography, 0.040 to 0.063 mm mesh (e.g. Merck Art 9385), where column elution was accelerated by an applied pressure of nitrogen at up to 5 p.s.i. Where thin layer chromatography (TLC) has been used it refers to silica gel TLC using 5×10 cm silica gel 60 $F_{254}$ plates (e.g. Merck Art 5719).

Where products were purified by preparative HPLC, this was carried out on a C18-reverse-phase column (1" Dynamax), eluting with a gradient of acetonitrile (containing 0.1% trifluoroacetic acid) in water (containing 0.1% trifluoroacetic acid) and the compounds isolated as their trifluoroacetate salts unless otherwise specified.

Standard Automated Preparative HPLC Column, Conditions & Eluent

Automated preparative high performance liquid chromatography (autoprep. HPLC) was carried out using a Supelco ABZ+5 μm 100 mm×22 mm i.d. column eluted with a mixture of solvents consisting of i) 0.1% formic acid in water and ii) 0.05% formic acid in acetonitrile, the eluent being expressed as the percentage of ii) in the solvent mixture, at a flow rate of 4 ml per minute. Unless otherwise stated the eluent was used as a gradient of 5–95% over 20 minutes.

LC/MS System

The Liquid Chromatography Mass Spectroscopy (LC/MS) systems used:

LC/MS System A—A Supelco ABZ+, 3.3 cm×4.6 mm i.d. column eluting with solvents: A—0.1% v/v formic acid+0.077% w/v ammonium acetate in water, and B—95:5 acetonitrile:water+0.05% v/v formic acid. The following gradient protocol was used: 100% A for 0.7 mins; A+B mixtures, gradient profile 0–100% B over 3.5 mins; hold at 100% B for 3.5 mins; return to 0% B over 0.3 mins. Positive and negative electrospray ionization was employed.

LC/MS System B—A Supelco ABZ+, 5 cm×2.1 mm i.d. column eluting with solvents: A—0.1% v/v formic acid+0.077% w/v ammonium acetate in water, and B—95:5 acetonitrile:water+0.05% v/v formic acid. The following gradient protocol was used: 0–100% B over 3.5 mins; hold at 100% B for 1.50 mins; return to 0% B over 0.50 mins. Positive and negative electrospray ionization was employed.

LC/MS System C—A Supelco ABZ+, 3.3 cm×4.6 mm i.d. column eluting with solvents: A—0.1% v/v formic acid+10 mmol ammonium acetate in water, and B—95:5 acetonitrile:water+0.05% v/v formic acid. The following gradient protocol was used: 100% A for 0.7 mins; A+B mixtures, gradient profile 0–100% B over 3.7 mins; hold at 100% B for 0.9 mins; return to 0% B over 0.2 mins. Positive and negative electrospray ionization was employed.

Example of Novel Process

Intermediate A: 2-Bromohypoxanthine

This compound is prepared from 2-thioxanthine** through oxidation of the mercapto group by bromine and in situ displacement by hydrobromine. For reference on the oxidation and displacement, see Beaman, A. G.; Gerster, J. F.; Robins, R. K, *J. Org. Chem*, 1962, 27, 986.1.

**Elion, G. B.; Lange, H. L., Hitchings, G. H., *J. Am. Chem. Soc.*, 1956, 78, 217.

Intermediate B: 2-[(1S)-1-benzyl-2-hydroxyethyl]amino-1,9-dihydro-6H-purin-6-one A mixture of 10.0 g (46.5 mmol) of Intermediate A and 14.1 g (93.0 mmol) of L-phenylalaninol in 30 mL of 2-methoxyethanol in an 100 mL round bottom flask was heated to reflux overnight (>12 h). The mixture was cooled to ambient temperature and gave rise to precipitation of solids. Additional precipitation was generated by addition of 150 mL of water. After being stirred for 1 h, the suspension was filtered and the filter cake was washed with 50 mL of water and dried under vacuum to afford 7.40 g (56%) of title compound as a yellow solid. The product was a mixture of two tautomers by $^1$H NMR. The combined filtrate and washing were allowed to stand at ambient temperature for two days. The resultant solids were filtered and dried to give 1.12 g (8.4%) of product as a white solid. The total yield was 64%. TLC (silica gel, 50% MeOH in $CH_2Cl_2$, 254 nm visualisation): Rf 0.9; 2-bromohypoxanthine Rf 0.6. MS (ES$^-$): m/z 284 (M–1)$^-$.

$^1$H NMR (major tautomer, 300 Mhz) δ2.76–2.98 (m, 2H), 3.49 (m, 2H), 4.09 (br s, 1H), 5.04 (2, 1H), 6.36 (d, J=8.1 Hz, 1H), 7.19–7.38 (m, 5H), 7.66 (s, 1H), 10.5 (s, 1H), 12.5 (s, 1H).

Intermediate C: (2S)-2-[(9-acetyl-6-oxo-6,9-dihydro-1H-purin-2-yl)amino]-3-phenylpropyl acetate To a suspension of 500 mg (1.75 mmol) of Intermediate B in 3.5 mL of DMF in a 25 mL round bottom flash was successively added 0.66 mL (7.02 mmol) of acetic anhydride, 5 mg (catalytic) of N,N-dimethylpyridine and 0.98 (7.02 mmol) of triethylamine at ambient temperature. The mixture was stirred at ambient temperature overnight. After being quenched with 15 mL of water and stirred for 2 h, the suspension was filtered and the filtering cake was washed with 10 mL of water, dried under vacuum at 70–100° C. to afford 470 mg (73%) of title compound as an off-white powder. TLC (silica gel, 10% MeOH in $CH_2Cl_2$, 254 nm visualisation): Rf 0.45. MS (ES$^-$): m/z 368 (M–1)$^-$, 326 (M–1–Ac)$^-$, 1H NMR (300 Mhz) δ1.96 (s, 3H), 2.80 (s, 3H), 2.90 (m, 2H),4.16 (m,2H), 4.37 (m, 1H), 6.70 (br s, 1H), 7.16–7.31 (m, 5H), 8.16 (s, 1H), 10.8 (s, 1H).

Intermediate D: (2S)-2-[(6-chloro-9H-purin-2-yl)amino]-3-phenylpropyl acetate

To 16.7 mL (179 mmol) of phosphorus oxychloride in a 100 mL round bottom flask was added 2.27 mL (17.9 mmol) of N,N-dimethylaniline at ambient temperature. The mixture was stirred for 10 min; then 4.40 g (11.9 mmol) of 6-hydroxypurine Intermediate C was added in two equal portions over 15 min. The mixture was heated at reflux for 15 min. After being cooled to ambient temperature, the mixture was slowly added to 550 mL of ice water with stirring. The aqueous mixture was neutralised to pH 3.5 by addition of solid NaOAc and extracted with $CH_2Cl_2$ (3×). The combined organic layers were washed with aqueous $NaHCO_3$ (2×), dried over anhydrous $Na_2SO_4$ and concentrated under vacuum. The resultant brown oil was chromatographed on silica gel. Elution with 5–10% MeOH in $CH_2Cl_2$ afforded 3.08 g (75%) of title compound as a brown solid. TLC (silica gel, 10% MeOH in $CH_2Cl_2$, 254 nm visualisation): Rf 0.50. MS (ES-): m/z 344 (M–1)–, 346 (M–1, isotope)–. 1H NMR (300 MHz) d 2.15 (s, 3H), 2.98 (m, 2H), 4.08–4.35 (m, 2H), 4.49 (m, 1H), 7.26–7.53 (m, 5H), 7.64 (br s, 1H), 8.25 (s, 1H), 13.1 (s, 1H).

Intermediate E: (2S)-2-[(6-amino-9H-purin-2-yl)amino]-3-phenyl-1-propanol

A 200 mL glass liner in a Parr pressure reactor was charged with 288 mg (0.834 mmol) of Intermediate D and 25 mL of 2M $NH_3$ in methanol. The reactor was sealed and heated at 90–100° C. for 16 h. After being cooled to ambient temperature, the solvent and excess reagent were evaporated under vacuum. Despite incomplete reaction as indicated by TLC, the resultant oil was chromatographed on silica gel. Elution with 10–15% MeOH in $CH_2Cl_2$ afforded 48 mg (20%) of title compound as a solid. Further elution afforded 156 mg (62%) of recovered starting material as the deacetylated form. TLC (silica gel, 10% MeOH in $CH_2Cl_2$, 254 nm visualisation): Rf 0.22. 1H NMR (300 MHz) d 2.61–2.80 (m, 2H), 3.30–3.45 (m, 2H), 3.95 (m, 1H), 4.70 (s, 1H), 5.65 (d, J=8.0 Hz), 6.41 (s, 2H), 6.99–7.26 (m, 5H), 7.52 (s, 1H), 12.1 (s, 1H).

Intermediate F: (3aS,4S,6R,6aR)-Methoxy-2,2-dimethyl-tetrahydro-furo[3,4-d][1,3]dioxole-4-carboxylic acid To a 1 L three neck round bottom flask equipped with an addition funnel, thermocouple probe and nitrogen inlet was added D-ribose (50 g) and acetone (400 mL). The mixture was cooled to −5° C. and then 2,2-dimethoxypropane (100 mL) followed by perchloric acid (20 mL) were added. The reaction mixture was allowed to warm to room temperature and then stirred for a brief period. Methanol (70 mL) was added and the reaction mixture was stirred overnight. The reaction solution was cooled to ca. 5° C. and ca. 95 mL of 30% sodium carbonate was added dropwise. The mixture was allowed to warm then filtered.

The resulting cake was washed with ethyl acetate (50 mL). The filtrate was concentrated in vacuo at ca. 200 mbar until 250 mL of residual volume remained, diluted with ethyl acetate (200 mL) and reconcentrated to a residual volume of 170 mL. Ethyl acetate (200 mL) and water (200 mL) were added and the phases were mixed and separated. The aqueous phase was washed twice with ethyl acetate (200 mL) and the layers were separated. The combined organic extracts were concentrated to a residual volume of 200 mL and rediluted with ethyl acetate (200 mL) to provide an ethyl acetate solution of 6R-methoxy-2,2-dimethyl-tetrahydro-(3aR,6aR)-furo[3,4-d][1,3]dioxol-4R-yl)-methanol.

To a 2 L three neck round bottom flask was added the ethyl acetate solution of 6R-methoxy-2,2-dimethyl-tetrahydro-(3aR,6aR)-furo[3,4-d][1,3]dioxol-4R-yl)-methanol, 6% sodium bicarbonate (158 mL) potassium bromide (2.3 g), and TEMPO (0.167 g). The reaction mixture was cooled to −7° C. Meanwhile, sodium bicarbonate (6.8 g) was dissolved into 10–13% sodium hypochlorite (400.5 mL). The bleach solution was added dropwise over ca. 40 minutes, keeping the temperature below 15° C. The reaction mixture was stirred for ca. 2 hours and 10% aqueous sodium sulfite solution (47 mL) was added. The reaction mixture was stirred for 15 minutes, the phases separated and the aqueous phase adjusted to pH 2 with 4M HCl and extracted twice with ethyl acetate (225 mL). The ethyl acetate extracts were concentrated in vacuo to provide a white residue which was triturated with cyclohexane (90 mL). The solids were filtered and dried in vacuo at 45° C. to provide title product (33.6 g) (46% yield re D-ribose) as a white solid: m.p. 126–129° C.

Intermediate G: (3aS,4S,6R,6aR)-6-Methoxy-2,2-dimethyl-tetrahydro-furo[3,4-d][1,3]dioxole-4-carboxylic acid amide To a 500 mL three neck round bottom flask was added Intermediate F (20 g) and ethyl acetate (160 mL) followed by thionyl chloride (9.4 mL). The reaction solution was warmed at 50° C. for 2 hours. Gaseous ammonia (16 g) was added at such a rate that the temperature remains between 40–60° C. Water (120 mL) was added. The layers were separated and the aqueous layer was washed twice with ethyl acetate (80 mL). The combined organic washes were concentrated in vacuo to dryness. The residue was triturated with cyclohexane (40 mL) and the solids filtered. The cake was washed with cyclohexane (40 mL) and the solids dried in vacuo at 45° C. to provide the title product (16.7 g) (83.9% yield) as a light tan solid: m.p. 134–136° C.; TLC (95/5 chloroform/methanol/~5 drops TFA per 50 mL/phosphomolybdic acid spray) rf=0.49.

Intermediate H: (3aS,4S,6R,6aR)-6-Methoxy-2,2-dimethyl-tetrahydro-furo[3,4-d][1,3]dioxole-4-carbonitrile To a 22 L three neck round bottom flask was added Intermediate G (643 g), ethyl acetate (7.72 L), N,N-dimethylformamide (1.26 L), and triethylamine (2.15 L). The reaction solution was cooled to ca. 0° C. and of then phosphorus oxychloride (1.38 L) was added at such a rate that the temperature was maintained below 25° C. The reaction was stirred for one and one-half hours. Aqueous potassium hydrogen carbonate (20%, 6.5 L) was added dropwise maintaining the temperature at or below 20° C. The layers were separated and the aqueous layer re-extracted with ethyl acetate (3.5 L). The combined organic layers were washed twice with 20% potassium hydrogen carbonate (3.5 L) and concentrated to a residual volume of ca. 1 L. Activated carbon (15 grams) was added to the thin oil and the mixture was filtered through celite (80 g). The cake was washed with ethyl acetate (100 mL). The filtrate was concentrated in vacuo to provide title product (519 g) (88% yield) as a reddish-orange oil: TLC (1:1 Ethyl acetate/cyclohexane; phosphomolybdic acid reagent development) rf=0.73.

Intermediate I: 5-(6R-Methoxy-2,2-dimethyl-tetrahydro-(3aR,6aR)-furo[3,4-d][1,3]dioxol-4R-yl)-1H-tetrazole To a 3 L three neck round bottom flask was added Intermediate H (200 g), toluene (2 L), azidotrimethylsilane (332 mL) and dibutyltin oxide (24.9 g). The reaction mixture was heated to 60° C. for 15 hours. The reaction mixture was concentrated in vacuo to a residual volume of ca. 300 mL. Toluene (1 L) was added and the solution was reconcentrated to a residual volume of ca. 470 mL. Toluene (400 mL) and water (19.8 mL) were added and the mixture was stirred at room temperature for approximately 2 hours. The mixture was concentrated to provide ca. 250 mL of residue. The residue was dissolved in toluene (800 mL) with warming then was allowed to cool to room temperature and was stirred for >3 days. The solids are filtered and washed twice with toluene (250 mL). The product was dried in vacuo to provide title product (135 g) (55% yield) as a white solid: mp 130° C.

Intermediate J: 2-Ethyl-5-(6R-methoxy-2,2-dimethyl-tetrahydro-(3aR,6aR)-furo[3,4-d][1,3]dioxol-4R-yl)-2H-tetrazole To a 1 L three neck round bottom flask was added Intermediate I (31.8 g), potassium carbonate (12.7 g) and acetone (238 mL). Ethyl iodide (14.1 mL) of was added via syringe and the reaction mixture was warmed at 42° C. for 2.5–3 hours. The reaction mixture was allowed to cool to room temperature and then cyclohexane (238 mL) was added. The resulting precipitate was filtered and the cake was washed three times with cyclohexane (65 mL). The filtrate was concentrated to a residual volume of 195 mL and then rediluted with cyclohexane (238 mL). The cyclohexane solution was cooled at 0–5° C. for 3 days and the resulting crystalline solid (N1 alkylation product) was filtered and washed three times with cyclohexane (65 mL). The combined filtrates was concentrated in vacuo to provide intermediate grade title product as an oil. The oil was dissolved in cyclohexane (200 mL) at 60° C. and the solution allowed to cool to room temperature and filtered. The resulting crystalline solid was filtered and washed three times with cyclohexane (65 mL). The combined filtrate was concentrated to provide title product as a yellow oil: TLC (1:1 Ethyl acetate/hexanes; phosphomolybdic acid reagent visualisation) rf=0.68.

Intermediate K: rel-Acetic acid 4R,5-diacetoxy-2R-(2-ethyl-2H-tetrazol-5-yl)-tetrahydro-furan-3R-yl ester To a round bottom flask was added Intermediate J (5.0 g). A solution of acetyl chloride (0.73 g) in methanol (50 mL)

was added to the flask and the reaction solution was heated to reflux at 300 mbar pressure. The reaction was distilled over an 8–9 hour period and methanol (135 mL) was added portionwise during this time to replenish the reaction volume. The reaction mixture was allowed to cool to room temperature and pyridine (15 mL) was added. The mixture was concentrated in vacuo and rediluted with pyridine. Ethyl acetate (25 mL) and acetic anhydride (6.6 g) were added to the pyridine solution and the resulting mixture stirred overnight at room temperature. The reaction mixture was cooled to 5–10° C. and approximately 2M sulfuric acid (ca 45 mL)was added dropwise over 20 minutes while maintaining the temperature below 10° C. The layers were separated and the organic layer was washed with approximately 0.7M sulfuric acid (ca 25 mL). The organic layer was washed with sat. sodium bicarbonate and brine and then concentrated in vacuo to provide a pale yellow oil that was dissolved in 50 mL of ethyl acetate. Acetic anhydride (3.04 g) and of concentrated sulfuric acid (0.65 g) were added and the reaction mixture was warmed to 50° C. for ca. 3.5 hours. The reaction was quenched with saturated sodium bicarbonate solution (25 mL). The organic layer was concentrated in vacuo to provide title product ((5.1 g) (82% yield) as a yellow oil: TLC (1:1 Ethyl acetate/hexanes; phosphomolybdic acid reagent visualisation) rf=0.44.

Intermediate L: (2R,3S,4S,5R)-4-(acetyloxy)-2-(6-amino-2-[(1S)-1-benzyl-2-hydroxyethyl]amino-9H-purin-9-yl)-5-(2-ethyl-2H-1,2,3,4-tetraazol-5-yl) tetrahydro-3-furanyl acetate To a mixture of 65 mg (0.19 mmol) of Intermediate K and 45 mg (0.16 mmol) of Intermediate E in 2.5 mL of MeCN in a 10 mL round bottom flask was successively added 88 mL (0.36 mmol) of N,O-bis(trimethylsilyl)acetamide and 34 mL (0.19 mmol) of trimethylsilyl trifluoromethanesulfonate at ambient temperature. The yellow suspension was heated to reflux and became a dark yellow solution. After being heated at reflux for 5 h, the mixture was cooled to ambient temperature, quenched with 2 mL of 10% $KHCO_3$ and extracted with $CH_2Cl_2$ (2×8 mL). The combined organic layers were washed with 10% brine (3 mL) and evaporated under vacuum. The resultant yellow foam was chromatographed on silica gel. Elution with 5% MeOH in $CH_2Cl_2$ afforded 70 mg (78%) of title compound as a solid. Despite low purity, the material was used for the next step without further purification. TLC (silica gel, 10% MeOH in $CH_2Cl_2$, 254 nm visualisation): Rf 0.54.

Example A (2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol A mixture of 70 mg (0.12 mmol) of Intermediate L and 20 mg (0.15 mmol) of anhydrous $K_2CO_3$ in 5 mL of methanol was stirred at ambient temperature for 2.5 h. The mixture was evaporated to near dryness, diluted with 2 mL of water and extracted with EtOAc (3×5 mL). The combined organic layers were dried with $Na_2SO_4$ and evaporated under vacuum. The resultant crude product was chromatographed on silica gel. Elution with 10% MeOH in $CH_2Cl_2$ afforded 24.5 mg (41%) of title compound as a solid.

TLC (silica gel, 10% MeOH in $CH_2Cl_2$, 254 nm visualisation): Rf 0.35.

Novel Examples

Intermediates

Intermediate 1: 2-Benzyl-5-(6-methoxy-2,2-dimethyl-tetrahydro-(3aR,6aR)-furo[3,4-d][1,3]dioxol-4R-yl)-2H-tetrazole To a stirred solution of Intermediate 10 (10 g, 41.3 mM) in dimethylformamide(50 ml) under nitrogen was added potassium carbonate(5.7 g, 41.3 mM) followed by benzyl bromide (6 ml,49.6 mM). The mixture was stirred at room temperature 18 hours. Water(100 ml) was added and the mixture was extracted with ethyl acetate(2×100 ml). The organic phases were combined, washed with water, brine and dried with magnesium sulphate. The residue, obtained after evaporation under reduced pressure was purified by column chromatography on flash silica eluted with 20% ethyl acetate/cyclohexane yielding the title compound as a waxy solid (2.98 g).

TLC $SiO_2$ (20% ethyl acetate in cyclohexane) Rf=0.45

Intermediate 2: Acetic acid 4R,5-diacetoxy-2R-(2-benzyl-2H-tetrazol-5-yl)-tetrahydro-furan-3R-yl ester To Intermediate 1 (2.98 g,8.9 mM) was added a mixture of TFA/Water(40 ml/4 ml) at room temperature and stirred for 1 hour. The mixture was evaporated under reduced pressure, azeotroped with toluene (3×20 ml). The residue was taken up into dichloromethane (100 ml) and dimethylaminopyridine(catalytic) and triethylamine(40 ml,356 mM) was added. The mixture was cooled to 0° C. and acetic anhydride (17 ml, 166 mM) was added dropwise over 15 m. The mixture was allowed to warm to room temperature and stirred for 16 h. The mixture was evaporated under reduced pressure and purified by column chromatography on flash silica eluted with 50% ethyl acetate/cyclohexane yielding the title compound as a as an oil (2.44 g).

LC/MS System A Rt=3.39 min, m/z=279 (MH+).

Intermediate 3: Acetic acid 4R-acetoxy-5R-(2-benzyl-2H-tetrazol-5-yl)-2R-(2,6-dichloro-purin-9-yl)-tetrahydro-furan-3R-yl ester To a stirred solution of Intermediate 2 (2.43 g, 6 mM) under nitrogen in acetonitrile (18 ml) was added 1,8-diazobicyclo[5,4,0]undec-7ene(1.35 ml, 9 mM) followed by 2,6-dichloropurine(1.5 g). The mixture was cooled to 0° C. and trimethylsilyltriflate (1.87 ml, 10.2 mM) was added dropwise over 15 m., allowed to warm to 20 C. and stirred for 38 h. The reaction mixture was quenched with aqueous saturated sodium hydrogen carbonate (35 ml) and extracted with ethyl acetate (3×50 ml). The organics were combined and washed with water (50 ml), dried with magnesium sulphate and evaporated under reduced pressure. The residue obtained was purified by column chromatography on flash silica eluted with 30% ethyl acetate/cyclohexane yielding the title compound as a as an oil (2.36 g). LC/MS System B Rt=3.43 min, m/z=535 (MH+).

Intermediate 4: Acetic acid 4R-acetoxy-5R-(2-benzyl-2H-tetrazol-5-yl)-2R-[2-chloro-6-(2,2-diphenyl-ethylamino)-purin-9-yl]-tetrahydro-furan-3R-yl ester To a stirred solution of Intermediate 3 (2.3 g, 4.3 mM) under nitrogen in isopropanol (40 ml) was added diisopropylethylamine(1.12 ml, 6.5 mM) followed by diphenylethyl amine(1.02 g, 5.2 mM), the resultant mixture was heated to 50° C. for 18 hours. The reaction mixture was evaporated under reduced pressure and the residue obtained purified by column chromatography on flash silica eluted with 50% ethyl acetate/cyclohexane yielding the title compound as a as an off white solid (2.9 g). LC/MS System B Rt=3.68 min, m/z=694 (MH+).

Intermediate 5: (2R,3S,4R,5R)-2-(2-Benzyl-2H-tetrazol-5-yl)-5-[6-(2,2-diphenyl-ethylamino)-2-(2-piperidin-1-yl-ethylamino)-purin-9-yl]-tetrahydro-furan-3,4-diol A solution of Intermediate 4 (2.9 g, 4.2 mM) and 2-piperidinoethylamine (3 ml, 20.9 mM) in dimethylsulfoxide(1 ml) under nitrogen was heated to 90° C. for 72 h. The mixture was allowed to cool and purified by column chromatography on flash silica eluted with 20% methanol, 79% chloroform and 1% ammonia yielding the title compound as a as an oil (1.6 g). LC/MS System A Rt=3.86 min, m/z=702 (MH+).

Intermediate 6: (2R,3S,4R,5R)-2-(2H-tetrazol-5-yl)-5-[6-(2,2-diphenyl-ethylamino)-2-(2-piperidin-1-yl-ethylamino)-purin-9-yl]-tetrahydro-furan-3,4-diol)

To 10% palladium on carbon (1.6 g) under nitrogen was added a solution of Intermediate 5 (1.67 g, 2.38 mM) in ethanol (50 ml) followed by ammonium formate (0.72 g, 11.9 mM). The mixture was heated to 50° C. for 4 h., filtered through a pad of Harborlite®. The filtrate was evaporated under reduced pressure to yield the title compound as a pale yellow solid (1.45 g).

LC/MS System A Rt=3.66 min, mz=612 (MH+).

Intermediate 7: (3aS,4S,6R,6aR)-Methoxy-2,2-dimethyl-tetrahydro-furo[3,4-d][1,3]dioxole-4-carboxylic acid To a 1 L three neck round bottom flask equipped with an addition funnel, thermocouple probe and nitrogen inlet was added D-ribose (50 g) and acetone (400 mL). The mixture was cooled to −5° C. and then 2,2-dimethoxypropane (100 mL) followed by perchloric acid (20 mL) were added. The reaction mixture was allowed to warm to room temperature and then stirred for a brief period. Methanol (70 mL) was added and the reaction mixture was stirred overnight. The reaction solution was cooled to ca. 5° C. and ca. 95 mL of 30% sodium carbonate was added dropwise. The mixture was allowed to warm then filtered. The resulting cake was washed with ethyl acetate (50 mL). The filtrate was concentrated in vacuo at ca. 200 mbar until 250 mL of residual volume remained, diluted with ethyl acetate (200 mL) and reconcentrated to a residual volume of 170 mL. Ethyl acetate (200 mL) and water (200 mL) were added and the phases were mixed and separated. The aqueous phase was washed twice with ethyl acetate (200 mL) and the layers were separated. The combined organic extracts were concentrated to a residual volume of 200 mL and rediluted with ethyl acetate (200 mL) to provide an ethyl acetate solution of 6R-methoxy-2,2-dimethyl-tetrahydro-(3aR,6aR)-furo[3,4-d][1,3]dioxol-4R-yl)-methanol.

To a 2 L three neck round bottom flask was added the ethyl acetate solution of 6R-methoxy-2,2-dimethyl-tetrahydro-(3aR,6aR)-furo[3,4-d][1,3]dioxol-4R-yl)-methanol, 6% sodium bicarbonate (158 mL) potassium bromide (2.3 g), and TEMPO (0.167 g). The reaction mixture was cooled to −7° C. Meanwhile, sodium bicarbonate (6.8 g) was dissolved into 10–13% sodium hypochlorite (400.5 mL). The bleach solution was added dropwise over ca. 40 minutes, keeping the temperature below 15° C. The reaction mixture was stirred for ca. 2 hours and 10% aqueous sodium sulfite solution (47 mL) was added. The reaction mixture was stirred for 15 minutes, the phases separated and the aqueous phase adjusted to pH 2 with 4M HCl and extracted twice with ethyl acetate (225 mL). The ethyl acetate extracts were concentrated in vacuo to provide a white residue which was triturated with cyclohexane (90 mL). The solids were filtered and dried in vacuo at 45° C. to provide title product (33.6 g) (46% yield re D-ribose) as a white solid: m.p. 126–129° C.

Intermediate 8 (3aS,4S,6R,6aR)-6-Methoxy-2,2-dimethyl-tetrahydro-furo[3,4-d][1,3]dioxole-4-carboxylic acid amide To a 500 mL three neck round bottom flask was added Intermediate 1 (20 g) and ethyl acetate (160 mL) followed by thionyl chloride (9.4 mL). The reaction solution was warmed at 50° C. for 2 hours. Gaseous ammonia (16 g) was added at such a rate that the temperature remains between 40–60° C. Water (120 mL) was added. The layers were separated and the aqueous layer was washed twice with ethyl acetate (80 mL). The combined organic washes were concentrated in vacuo to dryness. The residue was triturated with cyclohexane (40 mL) and the solids filtered. The cake was washed with cyclohexane (40 mL) and the solids dried in vacuo at 45° C. to provide the title product (16.7 g) (83.9% yield) as a light tan solid: m.p.=134–136° C.; TLC (95/5 chloroform/methanol/~5 drops TFA per 50 mL/phosphomolybdic acid spray) rf=0.49.

Intermediate 9: (3aS,4S,6R,6aR)-6-Methoxy-2,2-dimethyl-tetrahydro-furo[3,4-d][1,3]dioxole-4-carbonitrile To a 22 L three neck round bottom flask was added Intermediate 2 (643 g), ethyl acetate (7.72 L), N,N-dimethylformamide (1.26 L), and triethylamine (2.15 L). The reaction solution was cooled to ca. 0° C. and of then phosphorus oxychloride (1.38 L) was added at such a rate that the temperature was maintained below 25° C. The reaction was stirred for one and one-half hours. Aqueous potassium hydrogen carbonate (20%, 6.5 L) was added dropwise maintaining the temperature at or below 20° C. The layers were separated and the aqueous layer re-extracted with ethyl acetate (3.5 L). The combined organic layers were washed twice with 20% potassium hydrogen carbonate (3.5 L) and concentrated to a residual volume of ca. 1 L. Activated carbon (15 grams) was added to the thin oil and the mixture was filtered through celite (80 g). The cake was washed with ethyl acetate (100 mL). The filtrate was concentrated in vacuo to provide title product (519 g) (88% yield) as a reddish-orange oil: TLC (1:1 Ethyl acetate/cyclohexane; phosphomolybdic acid reagent development) rf=0.73.

Intermediate 10: 5-(6R-Methoxy-2,2-dimethyl-tetrahydro-(3aR ,6aR)-furo[3,4-d][1,3]dioxol-4R-yl)-1H-tetrazole To a 3 L three neck round bottom flask was added Intermediate 3 (200 g), toluene (2 L), azidotrimethylsilane (332 mL) and dibutyltin oxide (24.9 g). The reaction mixture was heated to 60° C. for 15 hours. The reaction mixture was concentrated in vacuo to a residual volume of ca. 300 mL. Toluene (1 L) was added and the solution was reconcentrated to a residual volume of ca. 470 mL.

Toluene (400 mL) and water (19.8 mL) were added and the mixture was stirred at room temperature for approximately 2 hours. The mixture was concentrated to provide ca. 250 mL of residue. The residue was dissolved in toluene (800 mL) with warming then was allowed to cool to room temperature and was stirred for >3 days. The solids are filtered and washed twice with toluene (250 mL). The product was dried in vacuo to provide title product (135 g) (55% yield) as a white solid: mp 130° C.

EXAMPLES

Example 1

2R,3R,4S,5R)-2-[6-(2,2-Diphenyl-ethylamino)-2-(2-piperidin-1-yl-ethylamino)-purin-9-yl]-5-[2-(3-hydroxy-propyl)-2H-tetrazol-5-yl]-tetrahydro-furan-3,4-diol bis(trifluoroacetate)

To a solution of Intermediate 6 (0.06 g, 0.098 mM) in dimethylformamide(1 ml) was added potassium carbonate (0.023 g, 0.167 mM) followed by 3-bromo-propanol (0.013 ml, 0.147 mM) in a sealed vial (eg Reacti-vial™), the reaction mixture stirred for 18 h. The mixture was filtered and the filtrate was evaporated under reduced pressure and purified using to preparative HPLC, (using a Capital column ODS2-IK5 15 mm×20 mm i.d, on a 30 min gradient of 5% to 95% acetonitrile containing 0.1% trifluoroacetic acid) to yield after freeze drying the title compound as a white solid (0.022 g) LC/MS System A Rt=3.59 min, m/z=670 (MH$^+$).

Example 2

2R,3R,4S,5R)-2-[6-(2,2-Diphenyl-ethylamino)-2-(2-piperidin-1-yl-ethylamino)-purin-9-yl]-5-(2-propyl-2H-tetrazo-5-tetrahydro-furan-3,4-diol bis(trifluoroacetate)

Example 2 was prepared in an analogous manner to Example 1 using 1-Bromopropane (0.013 ml, 0.147 mM) to yield after freeze drying the title compound as a white solid (0.026 g). LC/MS System A Rt=3.76 min, m/z=654 (MH$^+$).

Example 3

Acetic acid 2-(5-{5R-[6-(2,2-diphenyl-ethylamino)-2-(2-piperidin-1-yl-ethylamino)-purin-9-yl]-3S,4R-dihydroxy-tetrahydro-furan-2R -yl}-tetrazol-2-yl)-ethyl ester bis(trifluoroacetate)

Example 3 was prepared in an analogous manner to Example 1 using 2-bromoethyl acetate (0.017 ml, 0.147 mM) to yield after freeze drying the title compound as a white solid (0.029 g). LC/MS System A Rt=3.68 min, m/z=698 (MH$^+$).

Example 4

(2R,3S,4R,5R)-2-(2-Cyclopropylmethyl-2H-tetrazol-5-yl)-5-[6-(2,2-diphenyl-ethylamino)-2-(2-piperidin-1-yl-ethylamino)-purin-9-yl]-tetrahydro-furan-3,4-diol bis(trifluoroacetate)

Example 4 was prepared in an analogous manner to Example 1 using (Bromomethyl)cyclopropane (0.0165 ml, 0.147 mM) to yield after freeze drying the title compound as a white solid (0.023 g). LC/MS System A=3.74 min, m/z= 666 (MH$^+$).

Example 5

(2R,3R,4S,5R)-2-[6-(2,2-Diphenyl-ethylamino)-2-(2-piperidin-1-yl-ethylamino)-purin-9-yl]-5-[2-(2-hydroxy-ethyl)-2H-tetrazo-5-yl]-tetrahydro-furan-3,4-diol bis(trifluoroacetate)

To Example 3 (0.01 g) in methanol under nitrogen was added a solution of sodium methoxide (0.005 ml), the mixture was stirred at room temperature for 18 hours. The reaction mixture was evaporated under reduced pressure purified using to preparative HPLC, (using a Capital column ODS2-IK5 15 mm×20 mm i.d, on a 30 min gradient of 5% to 95% acetonitrile) yielding the title compound as a gum (0.006 g). LC/MS System C Rt=2.54 min, m/z=656 (MH$^+$).

Example 6

(2R,3S,4R,5R)-2-[2-(2-Chloro-ethyl)-2H-tetrazol-5-yl]-5-[6-(2,2-diphenyl-ethylamino)-2-(2-piperidin-1-yl-ethylamino)-purin-9-yl]-tetrahydro-furan-3,4-diol bis(trifluoroacetate)

Example 6 was prepared in an analogous manner to Example 1 using 1-Bromo-2-chloroethane (0.012 ml, 0.147 mM) to yield after freeze drying the title compound as a white solid (0.004 g). LC/MS System A=3.79 min, m/z=674 (M$^+$).

Example 7

(2R,3S,4R,5R)-2-(2-Cyclobutyl-2H-tetrazol-5-yl)-5-[6-(2,2-diphenyl-ethylamino)-2-(2-piperidin-1-yl-ethylamino)-purin-9-yl]-tetrahydro-furan-3,4-diol bis(trifluoroacetate)

Example 7 was prepared in an analogous manner to Example 1 using Bromocyclobutane (0.014 ml, 0.147 mM) to yield after freeze drying the title compound as a white solid (0.008 g). LC/MS System C=2.76 min, m/z=666 (MH$^+$).

Example 8

(2R,3S,4R,5R)-2-(2-Allyl 2H-tetrazol-5-[6-(2,2-diphenyl-ethylamino)-2-(2-piperidin-1-yl-ethylamino)-purin-9-yl]-tetrahydro-furan-3,4-diol bis(trifluoroacetate)

Example 8 was prepared in an analogous manner to Example 1 using allyl bromide (0.014 ml, 0.147 mM) at 0° C. and the mixture was then stirred at 0° C. for 3 h. to yield the title compound as a clear gum (0.004 g). LC/MS System C R$_t$=2.68 min,m/z=652 (MH$^+$).

Biological Data (A) Agonist Activity Against Receptor Sub-types

The compounds of the Examples were tested in screen (1) (agonist activity against receptor sub-types) and the results obtained were as follows:

| Example No | A2a | A1 | A3 |
|---|---|---|---|
| 1 | 22.64 | 434.8 | >93 |
| 2 | 30.95 | 755.4 | >93 |
| 3 | 16.59 | 310.5 | >93 |
| 4 | 37.24 | 1318.09 | >93 |
| 5 | 10.54 | 159.5 | >94 |
| 6 | 24.05 | 411.9 | >97 |
| 7 | 22.98 | 597.82 | >95 |
| 8 | 26.38 | >6131 | >165 |

Data are minimum values since preparation was found, after testing to contain an inactive impurity at around 20%.

Values given in the Table are EC$_{50}$ values as a ratio of that of NECA.

| ABBREVIATIONS | |
|---|---|
| TMS | trimethylsilyl |
| TFA | trifluoroacetic acid |
| DMF | N,N-dimethylformamide |
| NECA | N-ethylcarboxamideadenosine |
| DMAP | 4-dimethylaminopyridine |
| TEMPO | 2,2,6,6-tetramethyl-1-piperidinyloxy, free radical |
| TMSOTf | Trimethylsilyltrifluoromethylsulphonate |
| DBU | 1,8-diazabicyclo[5.4.0]undec-7-ene |
| BSA | bistrimethylsilylacetamide |
| DCM | dichloromethane |
| DAST | diethylaminosulphur trifluoride |
| Ph | phenyl |
| CDI | carbonyldiimidazole |
| NSAID | non-steroidal antiinflammatory drug |
| Bn | benzyl |

What is claimed is:

1. A compound of formula (I):

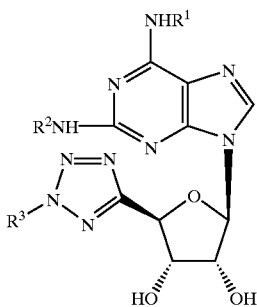

wherein
$R^1$ and $R^2$ independently represent a group selected from:
(i) $C_{3-8}$cycloalkyl-;
(ii) hydrogen;
(iii) aryl$_2$CHCH$_2$—;
(iv) $C_{3-8}$cycloalkyl$C_{1-6}$alkyl-;
(v) $C_{1-8}$alkyl-;
(vi) aryl$C_{1-6}$alkyl-;
(vii) $R^4R^5N$—$C_{1-6}$alkyl-;
(viii) $C_{1-6}$alkyl-CH(CH$_2$OH)—;
(ix) aryl$C_{1-5}$alkyl-CH(CH$_2$OH)—;
(x) aryl$C_{1-5}$alkyl-C(CH$_2$OH)$_2$—;
(xi) $C_{3-8}$cycloalkyl independently substituted by one or more —(CH$_2$)$_p$R$^6$ groups;
(xii) H$_2$NC(=NH)NHC$_{1-6}$alkyl-;
(xiii) a group of formula

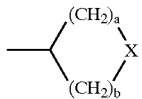

or such a group in which one methylene carbon atom adjacent to X, or both if such exist, is substituted by methyl;
(xiv) —C$_{1-6}$alkyl-OH;
(xv) —C$_{1-8}$haloalkyl;
(xvi) a group of formula

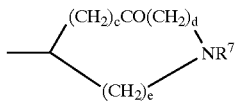

(xvii) aryl; and
(xviii) —(CH$_2$)$_f$SO$_2$NH$_g$(C$_{1-4}$alkyl-)$_{2-g}$ or —(CH$_2$)$_f$SO$_2$NH$_g$(arylC$_{1-4}$alkyl-)$_{2-g}$;
$R^3$ represents methyl, ethyl, —CH=CH$_2$, n-propyl, —CH$_2$CH=CH$_2$, —CH=CHCH$_3$, isopropyl, isopropenyl, cyclopropyl, cyclopropenyl, cyclopropylmethyl, cyclopropenylmethyl, cyclobutyl, cyclobutenyl, —(CH$_2$)$_q$halogen, —(CH$_2$)$_h$Y(CH$_2$)$_i$H, —(CH$_2$)$_h$COOCH$_3$, —(CH$_2$)$_h$OCOCH$_3$, —(CH$_2$)$_h$CON(CH$_2$)$_m$H((CH$_2$)$_n$H), —(CH$_2$)$_h$CO(CH$_2$)$_o$H or —CH$_2$C((CH$_2$)$_u$H)=NO(CH$_2$)$_v$H;
Y represents O, S or N(CH$_2$)$_j$;
a and b independently represent an integer 0 to 4 provided that a+b is in the range 3 to 5;
c, d and e independently represent an integer 0 to 3 provided that c+d+e is in the range 2 to 3;

f represents 2 or 3 and g represents an integer 0 to 2;
p represents 0 or 1;
q represents 2 or 3;
h represents 2 or 3;
i represents an integer 0 to 2 such that h+i is in the range 2 to 4
j represents an integer 0 to 2 such that h+i+j is in the range 2 to 4
m and n independently represent an integer 0 to 2 such that m+n is in the range 0 to 2;
o represents an integer 0 to 2 such that h+o is in the range 2 to 3;
u and v independently represent 0 or 1 such that u+v is in the range 0 to 1;
$R^4$ and $R^5$ independently represent hydrogen, $C_{1-6}$alkyl, aryl, arylC$_{1-6}$alkyl- or NR$^4$R$^5$ together may represent pyrrolidinyl, piperidinyl, morpholinyl, azetidinyl, azepinyl, piperazinyl or N—C1-6alkylpiperazinyl;
$R^6$ represents OH, NH$_2$, NHCOCH$_3$ or halogen;
$R^7$ represents hydrogen, C$_{1-6}$alkyl, C$_{1-6}$alkylaryl or —COC$_{1-6}$alkyl;
X represents NR$^7$, O, S, SO or SO$_2$;
provided that when $R^3$ represents methyl, ethyl or isopropyl then $R^1$ and/or $R^2$ independently must represent:
(a) —(CH$_2$)$_f$SO$_2$NH$_g$(C$_{1-4}$alkyl-)$_{2-g}$ or —(CH$_2$)$_f$SO$_2$NH$_g$(arylC$_{1-4}$alkyl-)$_{2-g}$ where f is 2 or 3 and g is an integer 0 to 2;
(b) $C_{3-8}$cycloalkyl independently substituted by one or more —(CH$_2$)$_p$NHCOCH$_3$ groups;
(c) a group of formula

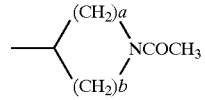

or such a group in which one methylene carbon atom adjacent to X, or both if such exist, is substituted by methyl;
(d) a group of formula

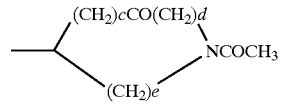

and salts and solvates thereof.

2. A compound of formula (I) according to claim 1 wherein $R^1$ and $R^2$ do not both represent hydrogen.

3. A compound according to claim 1 wherein $R^1$ represents aryl$_2$CHCH$_2$—, C$_{1-8}$alkyl, hydrogen or aryl C$_{1-6}$alkyl-.

4. A compound according to claim 1 wherein $R^1$ represents Ph$_2$CHCH$_2$—.

5. A compound according to claim 1 wherein $R^2$ represents R$^4$R$^5$N—C$_{1-6}$alkyl-, arylC$_{1-6}$alkyl-, arylC$_{1-5}$alkylCH(CH$_2$OH)—, aryl C$_{1-6}$ alkyl or C$_{1-6}$ alkyl-CH(CH$_2$OH)—.

6. A compound according to claim 1 wherein $R^2$ represents —(CH$_2$)$_2$(piperidin-1-yl).

7. A compound according to claim 1 wherein $R^3$ represents C$_{1-3}$alkyl, cyclobutyl, cyclopropylmethyl, —(CH$_2$)$_2$OCOCH$_3$, —(CH$_2$)$_{2-3}$OH or —(CH$_2$)$_2$halogen.

8. A compound according to claim 1 wherein $R^3$ represents n-propyl, 2-propenyl, cyclobutyl, cyclopropylmethyl, —(CH$_2$)$_2$OCOCH$_3$, or —(CH$_2$)$_{2-3}$OH.

9. A compound according to claim 1 wherein $R^4$ and $R^5$ independently represent hydrogen, $C_{1-6}$alkyl or aryl or $NR^4R^5$ together may represent pyrrolidinyl, piperidinyl, morpholinyl, azetidinyl, azepinyl, piperazinyl or N-methylpiperazinyl.

10. A compound according to claim 1 wherein $R^6$ represents OH or $NH_2$.

11. A compound according to claim 1 wherein X represents $NR^7$, O, S or $SO_2$.

12. A compound of the formula (I) according to claim 1 which is 2R,3R,4S,5R)-2-[6-(2,2-Diphenyl-ethylamino)-2-(2-piperidin-1-yl-ethylamino)-purin-9-yl]-5-[2-(3-hydroxy-propyl)-2H-tetrazol-5-yl]-tetrahydro-furan-3,4-diol;

2R,3R,4S,5R)-2-[6-(2,2-Diphenyl-ethylamino)-2-(2-piperidin-1-yl-ethylamino)-purin-9-yl]-5-(2propyl-2H-tetrazol-5-yl)-tetrahydro-furan-3,4-diol;

Acetic acid 2-(5-{5R-[6-(2,2-diphenyl-ethylamino)-2-(2-piperidin-1-yl-ethylamino)-purin-9-yl]-3S,4R-dihydroxy-tetrahydro-furan-2R-yl}-tetrazol-2yl)-ethyl ester;

(2R,3S,4R,5R)-2-(2-Cyclopropylmethyl-2H-tetrazol-5-yl)-5-[6-(2,2-diphenyl-ethylamino)-2-(2piperidin-1-yl-ethylamino)-purin-9-yl]-tetrahydro-furan-3,4-diol;

(2R,3R,4S,5R)-2-[6-(2,2-Diphenyl-ethylamino)-2-(2-piperidin-1-yl-ethylamino)-purin-9-yl]-5-[2-(2-hydroxy-ethyl)-2H-tetrazol-5-yl]-tetrahydro-furan-3,4-diol;

(2R,3S,4R,5R)-2-[2-(2-Chloro-ethyl)-2H-tetrazol-5-yl]-5-[6-(2,2-diphenyl-ethylamino)-2-(2-piperidin-1-yl-ethylamino)-purin-9-yl]-tetrahydro-furan-3,4-diol;

(2R,3S,4R,5R)-2-(2-Cyclobutyl-2H-tetrazol-5-yl)-5-[6-(2,2-diphenyl-ethylamino)-2-(2-piperidin-1-yl-ethylamino)-purin-9-yl]-tetrahydro-furan-3,4-diol;

(2R,3S,4R,5R)-2-(2-Allyl-2H-tetrazol-5-yl)-5-[6-(2,2-diphenyl-ethylamino)-2-(2-piperidin-1-yl-ethylamino)-purin-9-yl]-tetrahydro-furan-3,4diol;

or a salt or solvate of any thereof.

13. A pharmaceutical composition comprising a compound of formula (I) as defined in claim 1 or a physiologically acceptable salt or solvate thereof in admixture with one or more physiologically acceptable diluents or carriers.

14. A compound of formula (I) as defined claim 1 or a physiologically acceptable salt or solvate thereof for use as a pharmaceutical.

15. A method of treatment or prophylaxis of inflammatory diseases which comprises administering to a patient an effective amount of a compound of formula (I) as defined in claim 1 or a physiologically acceptable salt or solvate thereof.

16. A process for preparation of a compound of formula (I) as defined in claim 1 which comprises (a) reacting a corresponding compound of formula (II)

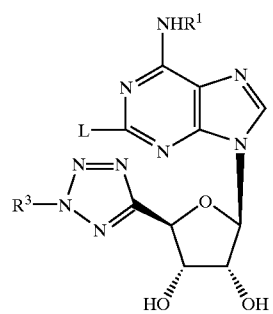

(II)

wherein L represents a leaving group or a protected derivative thereof with a compound of formula $R^2NH_2$ or a protected derivative thereof, wherein $R^1$, $R^2$ and $R^3$ are as defined in claim 1, or (b) preparing a compound of formula (I) in which $R^1$ represents hydrogen by reducing a compound of formula (III)

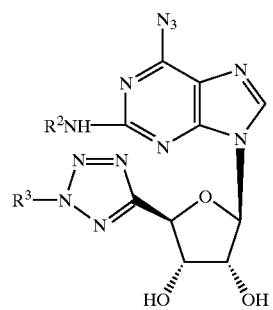

(III)

or a protected derivative thereof, wherein $R^2$ and $R^3$ are as defined in claim 1; or (d) deprotecting a compound of formula (I) which is protected; and where desired or necessary converting a compound of formula (I) or a salt thereof into another salt thereof.

17. A process for preparation of a compound of formula (I) as defined in claim 1 without the proviso which comprises (a) reacting a corresponding compound of formula (X)

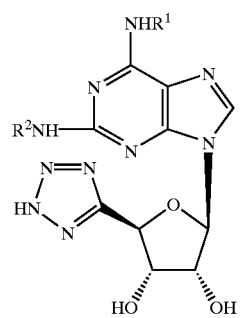

(X)

with a compound of formula (XI)

$R^3$—L     (XI)

wherein L is a leaving group and $R^1$, $R^2$ and $R^3$ are as defined in claim 1; or (b) reacting a corresponding compound of formula (XII)

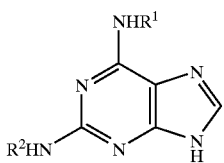

(XII)

with a compound of formula (V) or a protected derivative thereof, wherein $R^1$ and $R^2$ are as defined in claim 1.

18. A process according to claim 17 which is a process for preparing the compound (2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol and salts and solvates thereof.

19. A process according to claim 18 which comprises reacting a corresponding compound of formula

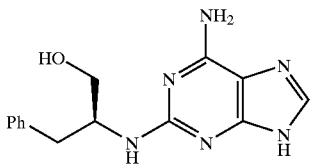

with a compound of formula

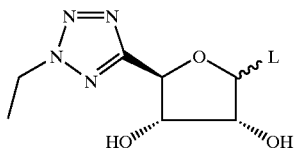

or a protected derivative thereof, wherein L is a leaving group.

20. A compound of formula (II)

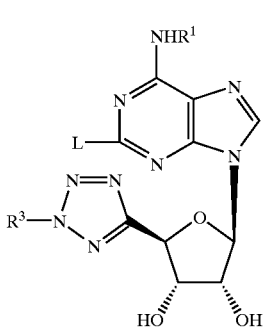

(II)

wherein L represents a leaving group and $R^1$ is as defined in claim 1, and $R^3$ represents n-propyl, 2-propenyl, cyclobutyl, cyclopropylmethyl, —(CH$_2$)$_2$OCOCH$_3$, or —(CH$_2$)$_{2-3}$OH or a protected derivative thereof.

21. A compound of formula (III)

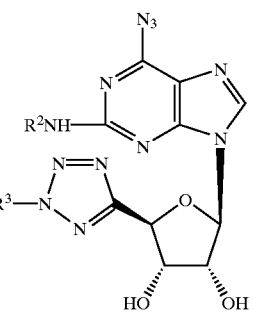

(III)

wherein $R^2$ is as defined in claim 1 and $R^3$ represents n-propyl, 2-propenyl, cyclobutyl, cyclopropylmethyl, —(CH$_2$)$_2$OCOCH$_3$, or —(CH$_2$)$_{2-3}$OH.

22. A compound of formula (IIIA)

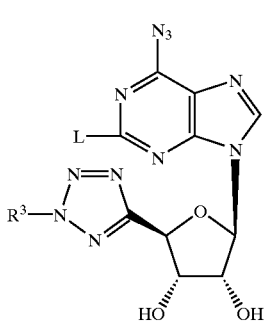

(IIIA)

wherein L represents a leaving group and $R^3$ represents n-propyl, 2-propenyl, cyclobutyl, cyclopropylmethyl, —(CH$_2$)$_2$OCOCH$_3$, or —(CH$_2$)$_{2-3}$OH or a protected derivative thereof.

23. A compound of formula (IV)

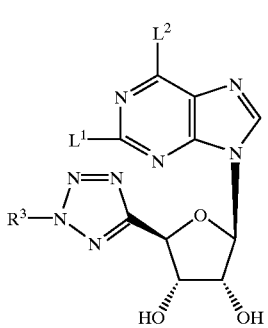

(IV)

wherein $L^1$ and $L^2$ independently represent a leaving group and $R^3$ represents n-propyl, 2-propenyl, cyclobutyl, cyclopropylmethyl, —(CH$_2$)$_2$OCOCH$_3$, or —(CH$_2$)$_{2-3}$OH or a protected derivative thereof.

24. A compound of formula (V)

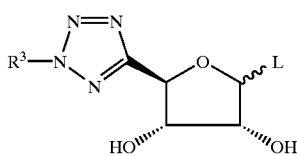
(V)

wherein L represents a leaving group and $R^3$ represents n-propyl, 2-propenyl, cyclobutyl, cyclopropylmethyl, —$(CH_2)_2OCOCH_3$, or —$(CH_2)_{2-3}OH$ or a protected derivative thereof.

25. A compound of formula (VI)

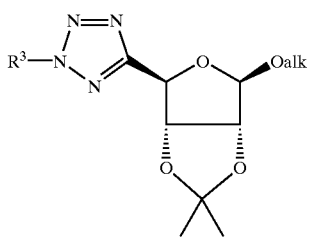
(VI)

wherein alk represents $C_{1-6}$ alkyl and $R^3$ represents n-propyl, 2-propenyl, cyclobutyl, cyclopropylmethyl, —$(CH_2)_2OCOCH_3$, or —$(CH_2)_{2-3}$ OH.

26. A compound of formula (X)

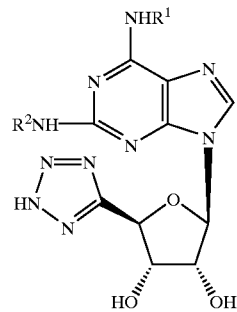
(X)

wherein $R^1$ and $R^2$ are as defined in claim 1 or a protected derivative thereof.

* * * * *